US007776922B2

(12) United States Patent
Brüggemeier et al.

(10) Patent No.: US 7,776,922 B2
(45) Date of Patent: Aug. 17, 2010

(54) SUBSTITUTED [(PHENYLETHANOYL)AMINO]BENZAMIDES

(75) Inventors: Ulf Brüggemeier, Leichlingen (DE); Petros Gatsios, Aachen (DE); Mark Meininghaus, Wuppertal (DE); Leila Telan, Düsseldorf (DE); Elisabeth Woltering, Hilden (DE); Martina Wuttke, Wuppertal (DE); Hartmut Beck, Köln (DE); Nils Griebenow, Dormagen (DE); Frank Süßmeier, Wuppertal (DE); Niels Svenstrup, Velbert (DE); Axel Kretschmer, Wuppertal (DE); Marcus Bauser, Wuppertal (DE); Johannes Köbberling, Grevenbroich (DE); Wahed Moradi, Monheim (DE); Siegfried Zaiss, Wuppertal (DE); Claudia Hirth-Dietrich, Wuppertal (DE); Barbara Albrecht, Wülfrath (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 280 days.

(21) Appl. No.: 11/791,144

(22) PCT Filed: Nov. 17, 2005

(86) PCT No.: PCT/EP2005/012322

§ 371 (c)(1),
(2), (4) Date: Nov. 26, 2007

(87) PCT Pub. No.: WO2006/053748

PCT Pub. Date: May 26, 2006

(65) Prior Publication Data

US 2008/0171786 A1     Jul. 17, 2008

(30) Foreign Application Priority Data

Nov. 20, 2004   (DE)   ........................ 10 2004 056 078
May 24, 2005    (DE)   ........................ 10 2005 023 834

(51) Int. Cl.
*A61K 31/165*  (2006.01)
*A61K 31/381*  (2006.01)
*A61K 31/357*  (2006.01)
*A61K 31/36*   (2006.01)
*A61K 31/47*   (2006.01)
*C07D 215/14*  (2006.01)
*C07D 317/60*  (2006.01)
*C07D 333/24*  (2006.01)
*C07D 333/60*  (2006.01)
*C07C 237/28*  (2006.01)

(52) U.S. Cl. .................. 514/616; 514/443; 514/438; 514/469; 514/466; 514/314; 564/158; 549/58; 549/77; 549/496; 549/441; 546/173

(58) Field of Classification Search ................ 514/443, 514/616, 438, 469, 466, 314; 549/58, 77, 549/496, 441; 546/173; 564/158
See application file for complete search history.

(56) References Cited

U.S. PATENT DOCUMENTS 6,548,514 B1    4/2003   Brown ........................ 514/277

FOREIGN PATENT DOCUMENTS

WO         0007980       2/2000

OTHER PUBLICATIONS

Von Der Thusen et al. Pharmacological Reviews 2003, 55(1), 133-166.*
Schafer et al. Drug Discovery Today 2008, 13 (21/22), 913-916.*
Horig et al. Journal of Translational Medicine 2004, 2(44).*
Byrn et al. Solid-State Chemistry of Drugs, 2d, Chapter 11 Hydrates and Solvates, 233-247, 233, 1999.*
Morissette et al. Adv. Drug Delivery Rev. 2004, 56, 275-300.*
A.M. Rouhi, Chem. & Eng. News, Feb. 24, 2003, 81(8), 32-35.*

* cited by examiner

*Primary Examiner*—Rebecca L Anderson
*Assistant Examiner*—Jason M Nolan
(74) *Attorney, Agent, or Firm*—Thomas C. Blankinship; Barbara A. Shimei

(57) ABSTRACT

The invention relates to substituted [(phenylethanoyl)amino] benzamides and methods for their preparation, and their use for the manufacture of medicaments for the treatment and/or prophylaxis of diseases, in particular of inflammatory disorders such as, for example, cutaneous, respiratory tract and cardiovascular disorders such as, for example, arteriosclerosis and coronary heart disease.

7 Claims, No Drawings

SUBSTITUTED [(PHENYLETHANOYL)AMINO]BENZAMIDES

The invention relates to substituted [(phenylethanoyl)amino]benzamides and methods for their preparation, and their use for the manufacture of medicaments for the treatment and/or prophylaxis of diseases, in particular of inflammatory disorders such as, for example, cutaneous, respiratory tract and cardiovascular disorders such as, for example, arteriosclerosis and coronary heart disease.

WO 02/070471 claims structurally similar compounds as factor Xa and factor VIIa inhibitors inter alia for the treatment of thrombosis, inflammatory disorders and arteriosclerosis.

WO 98/47885 claims structurally similar compounds as combined 5HT1A, 5HT1B and 5HT1D receptor antagonists for the treatment of disorders of the central nervous system.

The attraction of leukocytes to a specific site of the vasculature and the subsequent migration into the underlying damaged tissue form the basis of the development of inflammation. Besides the expression of various types of adhesion molecules (selectins, ICAM, VCAM) on the surface of leukocytes and the specific receptors on the surface of epithelial cells, it is the formation of a chemotactic gradient which is of outstanding importance for the attraction of leukocytes to the site of inflammation.

Interleukin-8 (IL-8) belongs to the class of proinflammatory chemokines with the ability to attract leukocytes. The role of IL-8 in various inflammatory disorders has been adequately described. The biological effects of IL-8 are mediated by binding to two specific receptors, CXCR1 and CXCR2, on the cell surface of target cells (Baggiolini M., *Annu Rev Immunol* 1997, 15, 675-705; Baggiolini M., *J Int Med* 2001, 250, 91-104).

The inflammatory component in the pathophysiology of arteriosclerosis is generally acknowledged. This is initiated equally by inflammatory cells (T cells, monocytes, macrophages) and secreted mediators (cytokines, chemokines) (Libby P., *Nature* 2002, 420, 868-874; Boisvert W. A., *Trends Cardiovasc Med* 2004, 14, 7-18). The inflammatory vascular lesions arise through reaction of monocytes which have migrated in with pathogenic lipoproteins in the arterial wall. The development of so-called "foam cells" from the monocytes which have migrated in through uptake of oxidized lipids in particular is of central importance in the development and stability of plaque. The production and effect of chemokines is extensively involved in the progress of this development of plaque. IL-8 in particular is responsible for the accumulation of lipid-loaded macrophages in atherosclerotic tissue (Boisvert W. A. et al, *J Clin Invest* 1998, 101, 353-363). In addition, there is increased expression of IL-8 and its specific receptor CXCR2 in atherosclerotic lesions.

An antagonist of the IL-8 receptor would stop accumulation of macrophages in the lesions and would thus be useful for treating arteriosclerosis.

In addition, IL-8 receptor antagonists could be used in any disease involving activated monocytes, macrophages or lymphocytes because all these cells express the receptor.

One object of the present invention is therefore to provide novel IL-8 receptor antagonists for the treatment of inflammatory disorders (especially cutaneous, respiratory tract and cardiovascular disorders) in humans and animals.

It has surprisingly been found that the [(phenylethanoyl)amino]benzamides described in the present invention are IL-8 receptor antagonists.

The invention relates to compounds of the formula

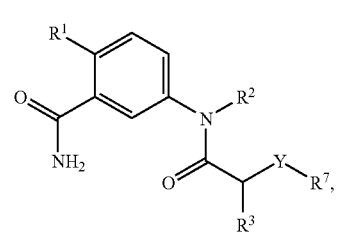

(Ia)

in which

Y is a bond, methanediyl, sulfur or oxygen, $R^1$ is biphenyl-4-yl, where 1 to 3 carbon atoms in biphenyl-4-yl may be replaced by nitrogen, or is 1,3-benzodioxol-5-yl or 2,3-dihydro-1,4-benzodioxin-5-yl, or is a group of the formula

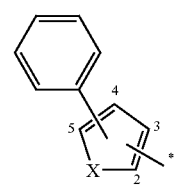

where

X is N, O or S,

* is the point of attachment to the carbon atom, and the phenyl ring is linked via position 4 or 5 when the five-membered ring is linked via position 2 to the carbon atom, or the phenyl ring is linked via position 5 when the five-membered ring is linked via position 3 to the carbon atom, or is naphth-1-yl or naphth-2-yl, where 1 carbon atom in naphth-1-yl and naphth-2-yl may be replaced by nitrogen, or is a group of the formula

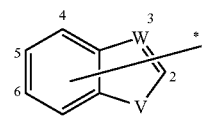

where

W is C or N,

V is N, O or S,

* is the point of attachment to the carbon atom, and the group is linked via position 2, 3, 5 or 6 to the carbon atom, or
is a group of the formula

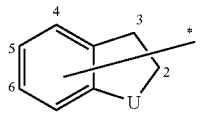

where
U is N, O or S,
* is the point of attachment to the carbon atom, and
the group is linked via position 2, 3, 5 or 6 to the carbon atom,
where the radicals $R^1$ may be substituted by 1 to 3 substituents, where the substituents are selected independently of one another from the group consisting of hydroxy, amino, halogen, cyano, trifluoromethyl, trifluoromethoxy, $C_1$-$C_6$-alkyl, $C_1$-$C_6$-alkoxy, $C_1$-$C_6$-alkylamino, hydroxycarbonyl, $C_1$-$C_6$-alkoxycarbonyl, aminocarbonyl, $C_1$-$C_6$-alkylaminocarbonyl, $C_1$-$C_6$-alkylcarbonyl and $C_1$-$C_6$-alkylcarbonylamino, $R^2$ is hydrogen, $C_1$-$C_6$-alkyl or $C_3$-$C_7$-cycloalkyl, $R^3$ is $C_3$-$C_7$-cycloalkyl or optionally up to pentafluoro-substituted $C_1$-$C_4$-alkyl, $R^7$ is a group of the formula

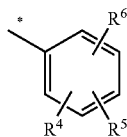

where
* is the point of attachment to Y,
$R^4$, $R^5$ and $R^6$ are independently of one another hydrogen, hydroxy, amino, halogen, cyano, trifluoromethyl, trifluoromethoxy, $C_1$-$C_6$-alkyl, $C_1$-$C_6$-alkoxy, $C_1$-$C_6$-alkylamino, $C_3$-$C_7$-cycloalkyl, 5- to 7-membered heterocyclyl, $C_6$-$C_{10}$-aryl, 5- or 6-membered heteroaryl, hydroxycarbonyl, $C_1$-$C_6$-alkoxycarbonyl, aminocarbonyl, $C_1$-$C_6$-alkylaminocarbonyl, $C_1$-$C_6$-alkylcarbonyl or $C_1$-$C_6$-alkylcarbonylamino,
in which cycloalkyl, heterocyclyl, aryl and heteroaryl may be substituted by 1 to 3 substituents, where the substituents are selected independently of one another from the group consisting of hydroxy, amino, halogen, cyano, trifluoromethyl, trifluoromethoxy, $C_1$-$C_6$-alkyl, $C_1$-$C_6$-alkoxy, $C_1$-$C_6$-alkylamino, hydroxycarbonyl, $C_1$-$C_6$-alkoxycarbonyl, aminocarbonyl, $C_1$-$C_6$-alkylaminocarbonyl, $C_1$-$C_6$-alkylcarbonyl and $C_1$-$C_6$-alkylcarbonylamino,
or
$R^4$ and $R^5$ are linked to adjacent carbon atoms and form a —O—$CH_2$—$CH_2$—O— bridge,
or
is a 5- or 6-membered heteroaryl,
in which heteroaryl may be substituted by 1 to 3 substituents, where the substituents are selected independently of one another from the group consisting of hydroxy, amino, halogen, cyano, trifluoromethyl, trifluoromethoxy, $C_1$-$C_6$-alkyl, $C_1$-$C_6$-alkoxy and $C_1$-$C_6$-alkylamino, and the salts thereof, the solvates thereof and the solvates of the salts thereof.

Compounds according to the invention are the compounds of the formula (Ia) and (I) and the salts, solvates and solvates of the salts thereof, compounds mentioned below as exemplary embodiment(s), and the salts, solvates and solvates of the salts thereof, insofar as the compounds encompassed by formula (Ia) and (I) and mentioned below are not already salts, solvates and solvates of the salts.

The compounds of the invention may, depending on their structure, exist in stereoisomeric forms (enantiomers, diastereomers). The invention therefore relates to the enantiomers or diastereomers and respective mixtures thereof. The stereoisomerically pure substituents can be isolated in a known manner from such mixtures of enantiomers and/or diastereomers.

Where the compounds of the invention can occur in tautomeric forms, the present invention encompasses all tautomeric forms.

Salts preferred for the purposes of the present invention are physiologically acceptable salts of the compounds of the invention. However, salts which are themselves unsuitable for pharmaceutical applications but can be used for example for isolating or purifying the compounds of the invention are also encompassed.

Physiologically acceptable salts of the compounds of the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of conventional bases such as, for example and preferably, alkali metal salts (e.g. sodium and potassium salts), alkaline earth metal salts (e.g. calcium and magnesium salts) and ammonium salts derived from ammonia or organic amines having 1 to 16 C atoms, such as, for example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refer for the purposes of the invention to those forms of the compounds of the invention which form a complex in the solid or liquid state through coordination with solvent molecules. Hydrates are a specific form of solvates in which the coordination takes place with water.

The free base of the salts of the compounds of the invention can be obtained for example by adding an aqueous base, for example dilute sodium hydroxide solution, and subsequent extraction with a solvent by methods known to the skilled worker.

For the purposes of the present invention, the substituents have, unless specified otherwise, the following meaning:

Alkyl per se and "alk" and "alkyl" in alkoxy, alkylamino, alkoxycarbonyl, alkylaminocarbonyl, alkylcarbonyl and alkylcarbonylamino stand for a linear or branched alkyl radical having usually 1 to 6, preferably 1 to 4, particularly preferably 1 to 3, carbon atoms, by way of example and preferably for methyl, ethyl, n-propyl, isopropyl, n-butyl, tert-butyl, n-pentyl and n-hexyl.

Alkoxy stands by way of example and preferably for methoxy, ethoxy, n-propoxy, isopropoxy, tert-butoxy, n-pentoxy and n-hexoxy.

Alkylamino stands for an alkylamino radical having one or two alkyl substituents (chosen independently of one another), by way of example and preferably for methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino. $C_1$-$C_3$-Alkylamino stands for example for a monoalkylamino radical having 1 to 3 carbon atoms or for a dialkylamino radical having 1 to 3 carbon atoms in each alkyl substituent.

Alkoxycarbonyl stands by way of example and preferably for methoxycarbonyl, ethoxycarbonyl, n-propoxycarbonyl, isopropoxycarbonyl, tert-butoxycarbonyl, n-pentoxycarbonyl and n-hexoxycarbonyl.

Alkylaminocarbonyl stands for an alkylaminocarbonyl radical having one or two alkyl substituents (chosen independently of one another), the alkyl substituents having, independently of one another, usually 1 to 6, preferably 1 to 4, particularly preferably 1 to 3 carbon atoms, by way of example and preferably for methylaminocarbonyl, ethylaminocarbonyl, n-propylaminocarbonyl, isopropylaminocarbonyl, tert-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-tert-butyl-N-methylaminocarbonyl, N-ethyl-N-n-pentylaminocarbonyl and N-n-hexyl-N-methylaminocarbonyl. $C_1$-$C_3$-Alkylaminocarbonyl stands for example for a monoalkylaminocarbonyl radical having 1 to 3 carbon atoms or for a dialkylaminocarbonyl radical having 1 to 3 carbon atoms in each alkyl substituent.

Alkylcarbonyl stands by way of example and preferably for methylcarbonyl, ethylcarbonyl, n-propylcarbonyl, isopropylcarbonyl, tert-butylcarbonyl, n-pentylcarbonyl and n-hexylcarbonyl.

Alkylcarbonylamino stands by way of example and preferably for methylcarbonylamino, ethylcarbonylamino, n-propylcarbonylamino, isopropylcarbonylamino, tert-butylcarbonylamino, n-pentylcarbonylamino and n-hexylcarbonylamino.

Cycloalkyl stands for a cycloalkyl group usually having 3 to 7, preferably 5 to 7 carbon atoms, by way of example and preferably mentioning cyclopropyl, cyclobutyl, cyclopentyl, cyclohexyl and cycloheptyl for cycloalkyl.

Aryl stands for a mono- or bicyclic aromatic radical usually having 6 to 10 carbon atoms, by way of example and preferably mentioning phenyl and naphthyl for aryl.

Heteroaryl stands for an aromatic, monocyclic radical usually having 5 or 6 ring atoms and up to 4, preferably up to 2, heteroatoms from the series S, O and N, where a nitrogen atom may also form an N-oxide, by way of example and preferably for thienyl, furyl, pyrrolyl, thiazolyl, oxazolyl, oxadiazolyl, pyrazolyl, imidazolyl, pyridyl, pyrimidyl, pyridazinyl, pyrazinyl.

Heterocyclyl stands for a monocyclic, heterocyclic radical usually having 5 to 7 ring atoms and up to 3, preferably up to 2, heteroatoms and/or hetero groups from the series N, O, S, SO, $SO_2$, where a nitrogen atom may also form an N-oxide. The heterocyclyl radicals may be saturated or partly unsaturated. 5- to 7-membered, monocyclic saturated heterocyclyl radicals having up to two heteroatoms from the series O, N and S are preferred, by way of example and preferably for pyrrolidin-2-yl, pyrrolidin-3-yl, pyrrolinyl, tetrahydrofuranyl, tetrahydrothienyl, pyranyl, piperidin-1-yl, piperidin-2-yl, piperidin-3-yl, piperidin-4-yl, thiopyranyl, morpholin-1-yl, morpholin-2-yl, morpholin-3-yl, perhydroazepinyl, piperazin-1-yl, piperazin-2-yl.

Halogen stands for fluorine, chlorine, bromine and iodine, preferably for fluorine and chlorine.

If radicals in the compounds of the invention are substituted, the radicals may, unless specified otherwise, be substituted one or more times, identically or differently. Substitution by up to three identical or different substituents is preferred. Substitution by one substituent is very particularly preferred.

Preference is given to compounds of the formula (Ia) which correspond to the formula

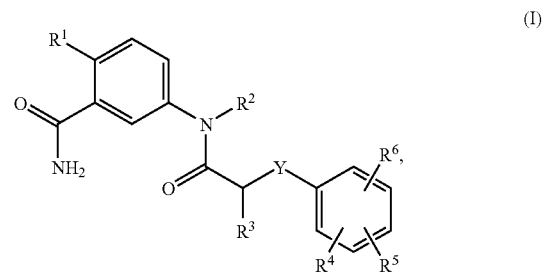

(I)

in which

Y is a bond or methanediyl, $R^1$ is biphenyl-4-yl, where 1 to 3 carbon atoms in biphenyl-4-yl may be replaced by nitrogen, or is 1,3-benzodioxol-5-yl or 2,3-dihydro-1,4-benzodioxin-5-yl, or is a group of the formula

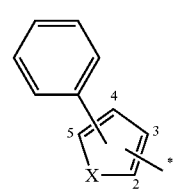

where

X is N, O or S,

* is the point of attachment to the carbon atom, and the phenyl ring is linked via position 4 or 5 when the five-membered ring is linked via position 2 to the carbon atom, or the phenyl ring is linked via position 5 when the five-membered ring is linked via position 3 to the carbon atom, or naphth-1-yl or naphth-2-yl, where 1 carbon atom in naphth-1-yl and naphth-2-yl may be replaced by nitrogen, or
is a group of the formula where
W is C or N,
V is N, O or S,
* is the point of attachment to the carbon atom, and
the group is linked via position 2, 3, 5 or 6 to the carbon atom,
or
is a group of the formula where
U is N, O or S,
* is the point of attachment to the carbon atom, and
the group is linked via position 2, 3, 5 or 6 to the carbon atom,
where the radicals $R^1$ may be substituted by 1 to 3 substituents, where the substituents are selected independently of one another from the group consisting of hydroxy, amino, halogen, cyano, trifluoromethyl, trifluoromethoxy, $C_1$-$C_6$-alkyl, $C_1$-$C_6$-alkoxy, $C_1$-$C_6$-alkylamino, hydroxycarbonyl, $C_1$-$C_6$-alkoxycarbonyl, aminocarbonyl, $C_1$-$C_6$-alkylaminocarbonyl, $C_1$-$C_6$-alkylcarbonyl and $C_1$-$C_6$-alkylcarbonylamino,
$R^2$ is hydrogen, $C_1$-$C_6$-alkyl or $C_3$-$C_7$-cycloalkyl,
$R^3$ is $C_3$-$C_7$-cycloalkyl or optionally up to pentafluoro-substituted $C_1$-$C_4$-alkyl,
$R^4$, $R^5$ and $R^6$ are independently of one another hydrogen, hydroxy, amino, halogen, cyano, trifluoromethyl, trifluoromethoxy, $C_1$-$C_6$-alkyl, $C_1$-$C_6$-alkoxy, $C_1$-$C_6$-alkylamino, $C_3$-$C_7$-cycloalkyl, 5- to 7-membered heterocyclyl, $C_6$-$C_{10}$-aryl, 5- or 6-membered heteroaryl, hydroxycarbonyl, $C_1$-$C_6$-alkoxycarbonyl, aminocarbonyl, $C_1$-$C_6$-alkylaminocarbonyl, $C_1$-$C_6$-alkylcarbonyl or $C_1$-$C_6$-alkylcarbonylamino,
in which cycloalkyl, heterocyclyl, aryl and heteroaryl may be substituted by 1 to 3 substituents, where the substituents are selected independently of one another from the group consisting of hydroxy, amino, halogen, cyano, trifluoromethyl, trifluoromethoxy, $C_1$-$C_6$-alkyl, $C_1$-$C_6$-alkoxy, $C_1$-$C_6$-alkylamino, hydroxycarbonyl, $C_1$-$C_6$-alkoxycarbonyl, aminocarbonyl, $C_1$-$C_6$-alkylaminocarbonyl, $C_1$-$C_6$-alkylcarbonyl and $C_1$-$C_6$-alkylcarbonylamino, and the salts thereof, the solvates thereof and the solvates of the salts thereof.

Preference is also given to compounds of the formula (I) in which
Y is a bond or methanediyl,
$R^1$ is biphenyl-4-yl, 1,3-benzodioxol-5-yl, 2,3-dihydro-1,4-benzodioxin-5-yl, 5-phenylthien-2-yl, 5-phenylfuran-2-yl, naphth-1-yl, naphth-2-yl, quinolin-6-yl, 1-benzothien-2-yl, 1-benzothien-3-yl, 1-benzothien-5-yl, 1-benzothien-6-yl, 1-benzofuran-2-yl or 1-benzofuran-3-yl,
where biphenyl-4-yl, 1,3-benzodioxol-5-yl, 2,3-dihydro-1,4-benzodioxin-5-yl, 5-phenylthien-2-yl, 5-phenylfuran-2-yl, naphth-1-yl, naphth-2-yl, quinolin-6-yl, 1-benzothien-2-yl, 1-benzothien-3-yl, 1-benzothien-5-yl, 1-benzothien-6-yl, 1-benzofuran-2-yl and 1-benzofuran-3-yl may be substituted by 1 to 3 substituents, where the substituents are selected independently of one another from the group consisting of hydroxy, amino, halogen, cyano, trifluoromethyl, trifluoromethoxy, $C_1$-$C_6$-alkyl, $C_1$-$C_6$-alkoxy, $C_1$-$C_6$-alkylamino, hydroxycarbonyl, $C_1$-$C_6$-alkoxycarbonyl, aminocarbonyl, $C_1$-$C_6$-alkylaminocarbonyl, $C_1$-$C_6$-alkylcarbonyl and $C_1$-$C_6$-alkylcarbonylamino,
$R^2$ is hydrogen or $C_1$-$C_6$-alkyl,
$R^3$ is $C_3$-$C_7$-cycloalkyl or optionally up to pentafluoro-substituted $C_1$-$C_4$-alkyl,
$R^4$, $R^5$ and $R^6$ are independently of one another hydrogen, hydroxy, amino, halogen, cyano, trifluoromethyl, trifluoromethoxy, $C_1$-$C_6$-alkyl, $C_1$-$C_6$-alkoxy, $C_1$-$C_6$-alkylamino, $C_3$-$C_7$-cycloalkyl, 5- to 7-membered heterocyclyl, $C_6$-$C_{10}$-aryl, 5- or 6-membered heteroaryl, hydroxycarbonyl, $C_1$-$C_6$-alkoxycarbonyl, aminocarbonyl, $C_1$-$C_6$-alkylaminocarbonyl, $C_1$-$C_6$-alkylcarbonyl or $C_1$-$C_6$-alkylcarbonylamino,
in which cycloalkyl, heterocyclyl, aryl and heteroaryl may be substituted by 1 to 3 substituents, where the substituents are selected independently of one another from the group consisting of hydroxy, amino, halogen, cyano, trifluoromethyl, trifluoromethoxy, $C_1$-$C_6$-alkyl, $C_1$-$C_6$-alkoxy, $C_1$-$C_6$-alkylamino, hydroxycarbonyl, $C_1$-$C_6$-alkoxycarbonyl, aminocarbonyl, $C_1$-$C_6$-alkylaminocarbonyl, $C_1$-$C_6$-alkylcarbonyl and $C_1$-$C_6$-alkylcarbonylamino, and the salts thereof, the solvates thereof and the solvates of the salts thereof.

Preference is also given to compounds of the formula (I) in which
Y is a bond or methanediyl,
$R^1$ is biphenyl-4-yl, 1,3-benzodioxol-5-yl, 2,3-dihydro-1,4-benzodioxin-5-yl, 5-phenylthien-2-yl, 5-phenylfuran-2-yl, naphth-1-yl, naphth-2-yl, quinolin-6-yl, 1-benzothien-2-yl, 1-benzothien-3-yl, 1-benzothien-5-yl, 1-benzothien-6-yl, 1-benzofuran-2-yl or 1-benzofuran-3-yl,
where biphenyl-4-yl, 1,3-benzodioxol-5-yl, 2,3-dihydro-1,4-benzodioxin-5-yl, 5-phenylthien-2-yl, 5-phenylfuran-2-yl, naphth-1-yl, naphth-2-yl, quinolin-6-yl, 1-benzothien-2-yl, 1-benzothien-3-yl, 1-benzothien-5-yl, 1-benzothien-6-yl, 1-benzofuran-2-yl and 1-benzofuran-3-yl may be substituted by 1 to 3 substituents, where the substituents are selected independently of one another from the group consisting of hydroxy, amino, halogen, cyano, trifluoromethyl, trifluoromethoxy, $C_1$-$C_6$-alkyl, $C_1$-$C_6$-alkoxy, $C_1$-$C_6$-alkylamino, hydroxycarbonyl, $C_1$-$C_6$-alkoxycarbonyl, aminocarbonyl, $C_1$-$C_6$-alkylaminocarbonyl, $C_1$-$C_6$-alkylcarbonyl and $C_1$-$C_6$-alkylcarbonylamino,
$R^2$ is hydrogen or $C_1$-$C_6$-alkyl,
$R^3$ is $C_3$-$C_7$-cycloalkyl or optionally up to pentafluoro-substituted $C_1$-$C_4$-alkyl,
$R^4$, $R^5$ and $R^6$ are independently of one another hydrogen, halogen, cyano, trifluoromethyl, trifluoromethoxy, $C_1$-$C_6$-alkyl, $C_3$-$C_7$-cycloalkyl, hydroxycarbonyl, $C_1$-$C_6$-alkoxycarbonyl, aminocarbonyl, $C_1$-$C_6$-alkylaminocarbonyl, $C_1$-$C_6$-alkylcarbonyl or $C_1$-$C_6$-alkylcarbonylamino, in which cycloalkyl may be substituted by 1 to 3 substituents, where the substituents are selected independently of one another from the group consisting of hydroxy, amino, halogen, cyano, trifluoromethyl, trifluoromethoxy, $C_1$-$C_6$-alkyl, $C_1$-$C_6$-alkoxy, $C_1$-$C_6$-alkylamino, hydroxycarbonyl, $C_1$-$C_6$-alkoxycarbonyl, aminocarbonyl, $C_1$-$C_6$-alkylaminocarbonyl, $C_1$-$C_6$-alkylcarbonyl and $C_1$-$C_6$-alkylcarbonylamino, and the salts thereof, the solvates thereof and the solvates of the salts thereof.

Preference is also given to compounds of the formula (I) in which

Y is a bond or methanediyl, $R^1$ for biphenyl-4-yl, 5-phenylthien-2-yl, naphth-2-yl, quinolin-6-yl, 1-benzothien-2-yl or 1-benzofuran-2-yl, where biphenyl-4-yl and naphth-2-yl may be substituted by 1 to 2 substituents, where the substituents are selected independently of one another from the group consisting of fluorine, chlorine, methoxy and ethoxy, $R^2$ is hydrogen, $R^3$ is methyl, ethyl or isopropyl, $R^4$, $R^5$ and $R^6$ are independently of one another hydrogen or halogen, and the salts thereof, the solvates thereof and the solvates of the salts thereof.

Preference is also given to compounds of the formula (I) or (Ia) in which Y is a bond or methanediyl.

Preference is also given to compounds of the formula (I) or (Ia) in which $R^1$ for biphenyl-4-yl, 5-phenylthien-2-yl, naphth-2-yl, quinolin-6-yl, 1-benzothien-2-yl or 1-benzofuran-2-yl, where biphenyl-4-yl and naphth-2-yl may be substituted by 1 to 2 substituents, where the substituents are selected independently of one another from the group consisting of fluorine, chlorine, methoxy and ethoxy.

Preference is also given to compounds of the formula (I) or (Ia) in which $R^2$ is hydrogen.

Preference is also given to compounds of the formula (I) or (Ia) in which $R^3$ is methyl, ethyl or isopropyl.

Preference is also given to compounds of the formula (I) in which $R^4$, $R^5$ and $R^6$ are independently of one another hydrogen or halogen.

Preference is also given to compounds of the formula (Ia) in which $R^7$ is triazolyl, thiazolyl, pyridyl, thienyl or furyl.

The invention further relates to a method for preparing the compounds of the formula (Ia), where

[A] compounds of the formula

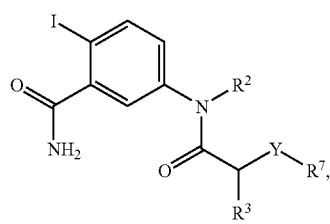
(II)

in which
Y, $R^2$, $R^3$ and $R^7$ have the meaning indicated above, are reacted with compounds of the formula

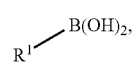
(III)

in which
$R^1$ has the meaning indicated above, or

[B] compounds of the formula

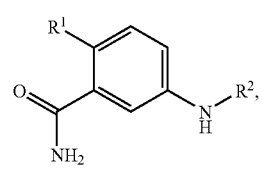
(IV)

in which
$R^1$ and $R^2$ have the meaning indicated above, are reacted with compounds of the formula

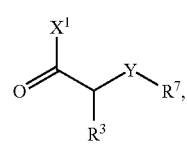
(V)

in which
Y, $R^3$ and $R^7$ have the meaning indicated above, and
$X^1$ is halogen, preferably iodine or bromine, or hydroxy.

The reaction by method [A] generally takes place under Suzuki reaction conditions in inert solvents, in the presence of a catalyst, where appropriate in the presence of an additional reagent, preferably in a temperature range from room temperature to 130° C. under atmospheric pressure (S. Kotha, K. Lahiri, D. Kashinath, *Tetrahedron* 2002, 58 (48), 9633-9695 and N. Miyaura, A. Suzuki, *Chem. Rev.* 1995, 95, 2457-2483).

Examples of catalysts are palladium catalysts usual for Suzuki reaction conditions, preferred catalysts being such as, for example, dichlorobis(triphenylphosphine)palladium, tetrakistriphenylphosphinepalladium(0), palladium(II) acetate, 1,1'-bis[(diphenylphosphino)ferrocene]palladium-II chloride (1:1) complex with dichloromethane.

Examples of additional reagents are potassium acetate, cesium, potassium or sodium carbonate, barium hydroxide, potassium tert-butoxide, cesium fluoride or potassium phosphate carried out, preferred additional reagents being such as, for example, potassium acetate and/or aqueous sodium carbonate solution.

Examples of inert solvents are ethers such as dioxane, tetrahydrofuran or 1,2-dimethoxyethane, hydrocarbons such as benzene, xylene or toluene, or other solvents such as nitrobenzene, dimethylformamide, dimethylacetamide, dimethyl sulfoxide or N-methylpyrrolidone, preferred solvents being such as, for example, dimethylformamide, dimethylacetamide, dimethyl sulfoxide or 1,2-dimethoxyethane.

The reaction by method [B] takes place if $X^1$ is halogen generally in inert solvents, in the presence of a base, preferably in a temperature range from 0° C. to 40° C. under atmospheric pressure.

Examples of inert solvents are halohydrocarbons such as methylene chloride, trichloromethane or 1,2-dichloroethane, ethers such as dioxane, tetrahydrofuran or 1,2-dimethoxyethane, or other solvents such as acetone, dimethylformamide, dimethylacetamide, 2-butanone or acetonitrile, with preference for tetrahydrofuran or methylene chloride.

Examples of bases are alkali metal carbonates such as cesium carbonate, sodium or potassium carbonate, or sodium or potassium methanolate, or sodium or potassium ethanolate or potassium tert-butoxide, or amides such as sodamide, lithium bis(trimethylsilyl)amide or lithium diisopropylamide, or other bases such as sodium hydride, DBU, triethylamine or diisopropylethylamine, with preference for diisopropylethylamine.

The reaction by method [B] takes place if $X^1$ is hydroxy generally in inert solvents, in the presence of dehydrating reagents, where appropriate in the presence of a base, preferably in a temperature range from 0° C. to room temperature under atmospheric pressure.

Examples of suitable dehydrating reagents in this connection are carbodiimides such as, for example, N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC) (where appropriate in the presence of pentafluorophenol (PFP)), N-cyclohexylcarbodiimide N'-propyloxymethylpolystyrene (PS-carbodiimide) or carbonyl compounds such as carbonyldiimidazole, or 1,2-oxazolium compounds such as 2-ethyl-5-phenyl-1,2-oxazolium 3-sulfate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxytri(dimethylamino) phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or mixtures thereof, with bases. The condensation is preferably carried out with HOBt and EDC.

Examples of bases are alkali metal carbonates such as, for example, sodium or potassium carbonate or bicarbonate, or organic bases such as trialkylamines, e.g. triethylamine, N-methylmorpholine, N-methylpiperidine, 4-dimethylaminopyridine or diisopropylethylamine. The condensation is preferably carried out with diisopropylethylamine.

Examples of inert solvents are halohydrocarbons such as dichloromethane or trichloromethane, hydrocarbon such as benzene, nitromethane, dioxane, dimethylformamide, acetonitrile or hexamethylphosphoric triamide. It is likewise possible to employ mixtures of the solvents. Dichloromethane or dimethylformamide is particularly preferred.

The compounds of the formulae (III) and (V) are known or can be synthesized by known methods from the appropriate precursors.

The compounds of the formula (II) are known or can be prepared by reacting compounds of the formula

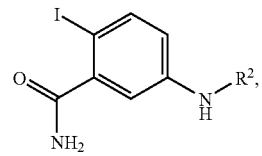

(VI)

in which $R^2$ has the meaning indicated above, with compounds of the formula (V) by method [B].

The compounds of the formula (VI) are known or can be prepared by reacting the compound of the formula

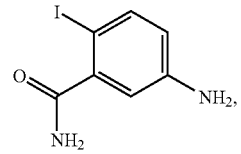

(VII)

with compounds of the formula

(VIII)

in which $R^2$ has the meaning indicated above, and $X^2$ is halogen, preferably iodine or bromine.

The reaction generally takes place in inert solvents, where appropriate in the presence of a base, where appropriate in the presence of potassium iodide, preferably in a temperature range from room temperature to reflux of the solvents under atmospheric pressure.

Examples of inert solvents are halohydrocarbons such as methylene chloride, trichloromethane or 1,2-dichloroethane, ethers such as dioxane, tetrahydrofuran or 1,2-dimethoxyethane, or other solvents such as acetone, dimethylformamide, dimethylacetamide, 2-butanone or acetonitrile, preferably tetrahydrofuran, methylene chloride, acetone, 2-butanone, acetonitrile, dimethylformamide or 1,2-dimethoxyethane.

Examples of bases are alkali metal carbonates such as cesium carbonate, sodium or potassium carbonate, or sodium or potassium methanolate, or sodium or potassium ethanolate or potassium tert-butoxide, or amides such as sodamide, lithium bis(trimethylsilyl)amide or lithium diisopropylamide, or organometallic compounds such as butyllithium or phenyllithium, or other bases such as sodium hydride, DBU, preferably potassium tert-butoxide, cesium carbonate, DBU, sodium hydride, potassium carbonate or sodium carbonate.

In an alternative method, the compounds of the formula (VI) can be prepared by reacting the compound of the formula (VII) with compounds of the formula

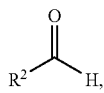
(IX)

in which

R² has the meaning indicated above, under conditions of reductive amination.

The reaction generally takes place in inert solvents, in the presence of a reducing agent, preferably in a temperature range from −20° C. to reflux of the solvents under atmospheric pressure.

Examples of inert solvents are halohydrocarbons such as methylene chloride, trichloromethane or 1,2-dichloroethane, alcohols such as methanol, ethanol, n-propanol, isopropanol, n-butanol or tert-butanol, or a mixture of alcohol and water, with preference for a mixture of methanol and water.

Examples of reducing agents are sodium borohydride or triacetoxyborohydride.

The compounds of the formula (IV) are known or can be prepared by reacting the compound of the formula (VI) with compounds of the formula (III) by method [A].

The amide function of the compounds of the formulae (II), (IV), (VI) and (VII) is, where appropriate, protected during the reactions with a polymeric support (e.g. Rink amide resin) or a protective group (e.g. 2,4-dimethoxybenzyl), which is eliminated in the last stage under conditions known to the skilled worker, in order to obtain compounds of the formula (I).

The compounds of the formulae (III), (V), (VII), (VIII) and (IX) are known or can be synthesized by known methods from the appropriate precursors.

The preparation of the compounds of the invention can be illustrated by the following synthesis scheme.

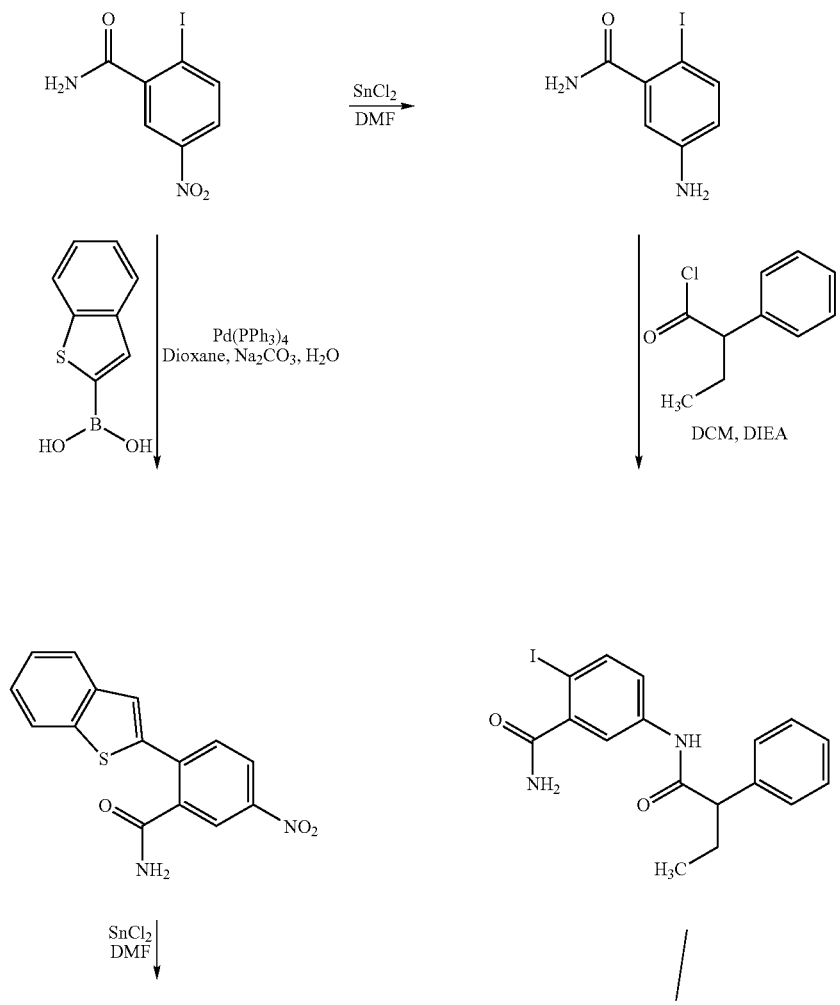

-continued

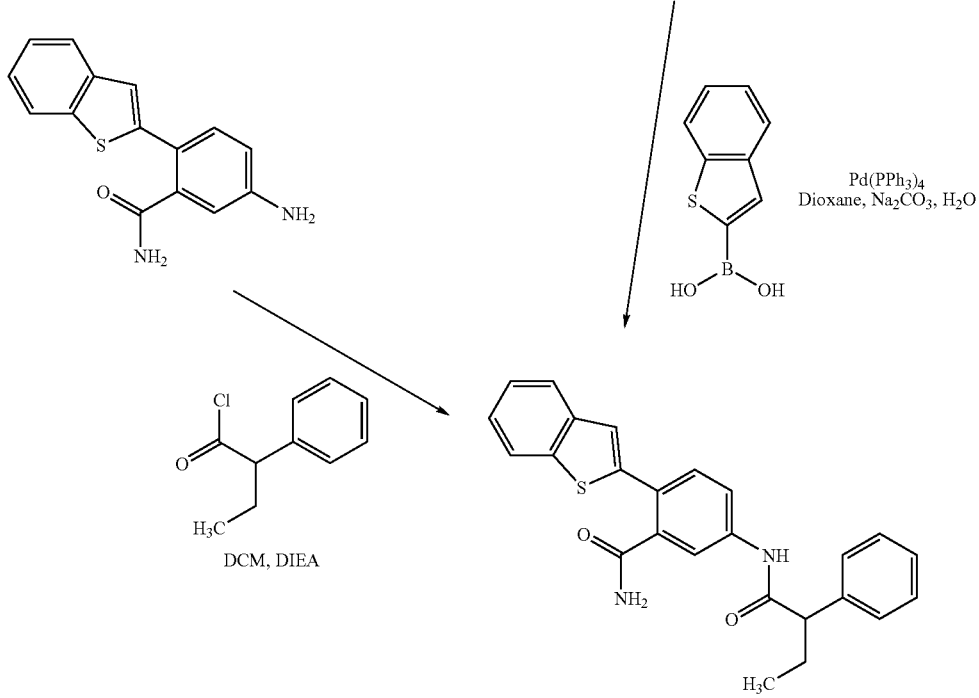

The compounds of the invention show a valuable range of pharmacological effects which could not have been predicted.

They are therefore suitable for use as medicaments for the treatment and/or prophylaxis of diseases in humans and animals.

The pharmaceutical activity of the compounds of the invention can be explained by their action as IL-8 receptor antagonists.

The present invention further relates to the use of the compounds of the invention for the treatment and/or prophylaxis of disorders, preferably of cutaneous, respiratory tract and cardiovascular disorders, especially of arteriosclerosis.

The compounds of the invention are suitable for the treatment and prevention of IL-8-induced inflammatory processes which include cutaneous disorders (e.g. psoriasis, (atopic) dermatitis, acne, eczemas), respiratory tract disorders (e.g. asthma, bronchitis, chronic obstructive lung disease, respiratory distress syndrome), cardiovascular disorders (e.g. arteriosclerosis, dyslipidemias, myocardial infarction, stroke, restenosis, reperfusion injury, thrombosis, ischemia, coronary heart diseases, (pulmonary) hypertension, (left/right) heart failure, arrhythmias, (stable/unstable) angina pectoris) and infections (e.g. with plasmodia, hepatitis viruses and herpes viruses), and arthritis (e.g. osteoarthritis, rheumatoid arthritis), osteoporosis, Crohn's disease, inflammatory bowel disease (e.g. ulcerative colitis), Alzheimer's disease, sepsis, gingivitis, shock (e.g. septic shock, endotoxic shock, gram-negative shock), renal failure, (glumerulo) nephritis, sinusitis, pancreatitis, meningitis, encephalitis, graft-host reaction, multiple sclerosis, hyperoxia-induced inflammations, autoimmune diseases, gout, allergies, fibrosis (e.g. liver fibrosis, pulmonary fibrosis, cystic fibrosis), edema formation, diabetes, emphysema and cancer (e.g. lung cancer, neoplasm).

The compounds of the invention can, on the basis of their pharmacological properties, be employed alone and, if required, also in combination with other active ingredients, in particular with antihyperlipidemic, antiarteriosclerotic, antidiabetic, antiinflammatory or antihypertensive active ingredients. Examples thereof are cholesterol synthesis inhibitors such as, for example, statins such as, for example, simvastatin, pravastatin and atorvastatin, antioxidants such as, for example, probucol, AGI1067 and Bo653, PPAR modulators, fibrates such as, for example, gemfibrozil and fenofibrate, cholesterol absorption inhibitors, such as, for example, ezetimibe, bile acid resins such as, for example, cholestyramine and colesevelam, acetylCoA acyltranferase (ACAT) inhibitors, cholesterol ester transfer protein (CETP) inhibitors, microsomal transfer protein (MTP)/apolipoproteinB secretion inhibitors, ileal bile acid transporter (IBAT) inhibitors, niacin and its slow-release forms, insulin (of animal, human or biotechnological origin and mixtures thereof), insulin sensitizers, calcium channel antagonists of, for example, the dihydropyridine type, diltiazem type and verapamil type, ACE inhibitors such as, for example, captropril, enalapril, ramipril and lisinopril, angiotensin II receptor antagonists such as, for example, valsartan, losartan and telmisartan, aldosterone receptor antagonists such as, for example, spironolactone and eplerenone, beta blockers such as, for example, atenolol, propanolol, bisoprolol and metoprolol, diuretics such as, for example, thiazides, potassium-sparing diuretics and loop diuretics, digitalis glycosides, nitrates or NO donors, such as, for example, isosorbide mononitrate, isosorbide dinitrate, aspirin, potassium supplement, antidiabetics such as, for example, sulfonylureas and biguanidines, CB1 antagonists, antiarrhythmics and non-steroidal antirheumatic drugs.

The present invention further relates to the use of the compounds of the invention for the treatment and/or prophylaxis of disorders, especially of the aforementioned disorders.

The present invention further relates to the use of the compounds of the invention for the manufacture of a medicament for the treatment and/or prophylaxis of disorders, especially of the aforementioned disorders.

The present invention further relates to interleukin-8 receptor antagonists for the treatment and/or prophylaxis of heart failure.

The present invention further relates to the use of an interleukin-8 receptor antagonist for the manufacture of a medicament for the treatment and/or prophylaxis of heart failure.

The present invention further relates to a method for the treatment and/or prophylaxis of disorders, especially of the aforementioned disorders, by using a therapeutically effective amount of the compounds of the invention.

The compounds of the invention can act systemically and/or locally. For this purpose, they can be administered in a suitable way such as, for example, by the oral, parenteral, pulmonary, nasal, sublingual, lingual, buccal, rectal, dermal, transdermal, conjunctival, otic route or as implant or stent.

The compounds of the invention can be administered in administration forms suitable for these administration routes.

Suitable for oral administration are administration forms which function according to the prior art and deliver the compounds of the invention rapidly and/or in modified fashion, and which contain the compounds of the invention in crystalline and/or amorphized and/or dissolved form, such as, for example, tablets (uncoated or coated tablets, for example having enteric coatings or coatings which are insoluble or dissolve with a delay and control the release of the compound of the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilizates or sterile powders.

Oral administration is preferred.

Suitable for the other administration routes are, for example, pharmaceutical forms for inhalation (inter alia powder inhalers, nebulizers), nasal drops, solutions, sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (such as, for example, patches), milk, pastes, foams, dusting powders, implants or stents.

The compounds of the invention can be converted into the stated administration forms. This can take place in a manner known per se by mixing with inert, nontoxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colors (e.g. inorganic pigments such as, for example, iron oxides) and masking flavors and/or odors.

The present invention further relates to medicaments which comprise at least one compound of the invention, normally together with one or more inert, nontoxic, pharmaceutically suitable excipients, and to the use thereof for the aforementioned purposes.

It has generally proved advantageous to administer on parenteral administration amounts of about 0.001 to 100 mg/kg of body weight every 24 hours to achieve effective results. On oral administration the amount is about 0.01 to 250 mg/kg of body weight every 24 hours. On dermal administration the amount is about 0.1 to 150 mg/kg of body weight every 24 hours.

It may nevertheless be necessary where appropriate to deviate from the stated amounts, in particular as a function of the bodyweight, route of administration, individual response to the active ingredient, nature of the preparation and time or interval over which administration takes place. Thus, it may be sufficient in some cases to make do with less than the aforementioned minimum amount, whereas in other cases the stated upper limit must be exceeded. It may in the event of administration of larger amounts be advisable to divide these into a plurality of individual doses over the day.

The percentage data in the following tests and examples are, unless indicated otherwise, percentages by weight; parts are parts by weight. Solvent ratios, dilution ratios and concentration data of liquid/liquid solutions are in each case based on volume. The statement "w/v" means "weight/volume". Thus, for example, "10% w/v" means: 100 ml of solution or suspension contain 10 g of substance.

A) EXAMPLES

| Abbreviations: | |
|---|---|
| Abs. | absolute |
| ATP | adenosine triphosphate |
| Boc | tert-butoxycarbonyl |
| BSA | *bovine* serum albumin |
| $CDCl_3$ | deuterochloroform |
| $CO_2$ | carbon dioxide |
| conc. | concentrated |
| DCM | dichloromethane |
| DIEA | N,N-diisopropylethylamine |
| DMEM | Dulbecco's Modified Essential Medium |
| DMSO | dimethyl sulfoxide |
| EDC | N'-(3-dimethylaminopropyl)-N-ethylcarbodiimide |
| EDTA | ethylenediaminetetraacetic acid |
| eq. | equivalent |
| ESI | electrospray ionization (in MS) |
| FCS | fetal calf serum |
| Fmoc | fluorenylmethoxycarbonyl |
| h | hour |
| HOBt | 1-hydroxy-1H-benzotriazole |
| HPLC | high pressure, high performance liquid chromatography |
| LC-MS | coupled liquid chromatography-mass spectroscopy |
| Min. | minutes |
| MS | mass spectroscopy |
| MW | molecular weight [g/mol] |
| NMR | nuclear magnetic resonance spectroscopy |
| PBS | phosphate buffered saline |
| PMNL | polymorphonuclear leukocytes |
| $R_f$ | retention index (in TLC) |
| RP-HPLC | reverse phase HPLC |
| RT | room temperature |
| $R_t$ | retention time (in HPLC) |
| sat. | saturated |
| TFA | trifluoroacetic acid |
| THF | tetrahydrofuran |
| TLC | thin-layer chromatography |

HPLC and LC-MS Methods:

Method 1 (HPLC): Instrument: HP 1100 with DAD detection; column: Kromasil RP-18, 60 mm×2 mm, 3.5 µm; eluent A: 5 ml HClO$_4$/l water, eluent B: acetonitrile; gradient: 0 min 2% B, 0.5 min 2% B, 4.5 min 90% B, 6.5 min 90% B; flow rate: 0.75 ml/min; oven: 30° C.; UV detection: 210 nm.

Method 2 (LC-MS): MS instrument type: Micromass ZQ; HPLC instrument type: HP 1100 series; UV DAD; column: Phenomenex Synergi 2µ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 3 (LC-MS): MS instrument: Micromass TOF (LCT); HPLC instrument: 2-column switching, Waters2690; column: YMC-ODS-AQ, 50 mm×4.6 mm, 3.0 µm; eluent A: water+0.1% formic acid, eluent B: acetonitrile+0.1% formic acid; gradient: 0.0 min 100% A→0.2 min 95% A→1.8 min 25% A→1.9 min 10% A→2.0 min 5% A→3.2 min 5% A; oven: 40° C.; flow rate: 3.0 ml/min; UV detection: 210 nm.

Method 4 (LC-MS): Instrument: Micromass Quattro LCZ with HPLC Agilent series 1100; column: Phenomenex Synergi 2µ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

Method 5 (LC-MS): MS instrument: Waters ZQ 2000; HPLC instrument: Agilent 1100, 2-column switching, Autosampler: HTC PAL; column: YMC-ODS-AQ, 50 mm×4.6 mm, 3.0 µm; eluent A: water+0.1% formic acid, eluent B: acetonitrile+0.1% formic acid; gradient: 0.0 min 100% A-0.1 min 95% A-0.8 min 25% A-0.9 min 5% A-1.8 min 5% A-1.81 min 100% A-1.9 min 100% A; oven: 40° C.; flow rate: 3.0 ml/min; UV detection: 210 nm.

Method 6 (LC-MS): MS instrument type: Micromass ZQ; HPLC instrument type: Waters Alliance 2795; column: Phenomenex Synergi 2µ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30%→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 7 (HPLC): Instrument: HP 1100 with DAD detection; column: Kromasil RP-18, 60 mm×2 mm, 3.5 µm; eluent A: 5 ml HClO$_4$/l water, eluent B: acetonitrile; gradient: 0 min 2% B, 0.5 min 2% B, 4.5 min 90% B, 9 min 90% B; flow rate: 0.75 ml/min; oven: 30° C.; UV detection: 210 nm.

General Procedures

General Procedure A: Preparation of Polymer 2

Polymer-bound 2-iodo-5-nitrobenzamide (polymer 1; Example 6A) is introduced into a 2:1 mixture of dioxane and aqueous sodium carbonate solution as solvent. 10 equivalents of the boronic acid and 0.1 equivalent of the Pd catalyst are added, and the mixture is stirred under argon at 80° C. overnight. Decantation is followed by washing three times with water, three times with DMF, twice with 0.1% strength sodium pyrrolidinethiocarbamate in a mixture of THF and methanol (5:1) as solvent and then three times each with methanol and DCM alternately. The polymer is subsequently dried in vacuo.

A test elimination with DCM/TFA 1:1 affords the corresponding primary nitrobenzamide.

General Procedure B: Preparation of Polymer 3

Polymer 2 is mixed with a 2-molar tin dichloride solution in DMF (65 equivalents) and shaken at RT overnight. Decantation is followed by washing three times each with DMF, methanol and DCM and drying in vacuo.

A test elimination with DCM/TFA 1:1 affords the corresponding aniline.

General Procedure C: Preparation of Polymer 4

Polymer 3 is introduced into DCM. 10 equivalents of DIEA and 5 equivalents of the carbonyl chloride are added, and the mixture is shaken at RT overnight. Decantation is followed by washing three times with DMF and then three times with methanol and DCM alternately, and the polymer is dried in vacuo. A 2:1 mixture of dioxane and a solution of 5 equivalents of potassium hydroxide in methanol is added, and the mixture is shaken at RT overnight. The polymer is filtered off and the polymer is washed three times with water and DMF and then three times with methanol and DCM alternately. The polymer is dried in vacuo.

General Procedure D: Elimination of the Product from Polymer 4

Polymer 4 is mixed with concentrated TFA. The mixture is left to stand for one hour and the polymer is filtered off. The polymer is then mixed with a 1:1 mixture of TFA and DCM and again left to stand for one hour. The polymer is again filtered off and the polymer is washed twice with the 1:1 mixture of TFA and DCM. The combined filtrates are evaporated in vacuo, and the crude product obtained in this way is purified by preparative HPLC.

Starting Compounds 2-(Het)arylacetic acids which are not commercially available can be synthesized by lithiation with LDA or LiHMTS and subsequent alkylation with an alkyl halide, see Thompson, H. W.; Rashid, S. Y. *J. Org. Chem.* 2002, 67, 2813-2825.

Example 1A

2-Iodo-5-nitrobenzoic acid

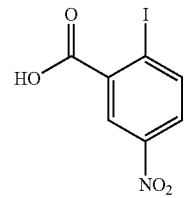

For preparation, compare for example N. G. Kundu, W. M. Khan, *Tetrahedron* 2000, 56 (27), 4777-4792.

HPLC (method 1): R$_t$=3.85 min.

$^1$H-NMR (400 MHz, DMSO-d$_6$): δ=8.02 (m, 1H), 8.30 (m, 1H), 8.41 (m, 1H), 13.95 (br. s, 1H).

Example 2A

2-Iodo-5-nitrobenzoyl chloride

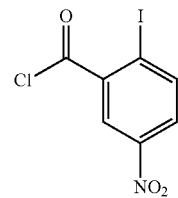

29.30 g (100 mmol) of 2-iodo-5-nitrobenzoic acid are suspended in a mixture of 200 ml of DCM and 1 ml of DMF as solvent. 19.04 g (150 mmol, 1.5 equivalents) of oxalyl chloride are slowly added dropwise at room temperature. The mixture is then stirred at room temperature for two hours and at 30° C. for 30 min. This is followed by evaporation in a rotary evaporator, and the resulting crude product is employed in the following stage.

Example 3A

2-Iodo-5-nitrobenzamide

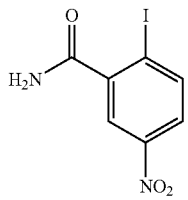

5.0 g (17 mmol) of the compound from Example 1A are suspended in 50 ml of dichloromethane. 2.44 g (20.5 mmol) of thionyl chloride are added, and the solution is heated under reflux overnight (16 h). The reaction mixture is concentrated and the residue is twice stirred with toluene and again concentrated in a rotary evaporator. The residue is suspended in 30 ml of dioxane and slowly added dropwise to a solution, cooled to 0° C., of 25% strength ammonia in water (50 ml). After addition of the acid chloride, the reaction mixture is stirred at 0° C. for 1 hour, and then warmed to room temperature and stirred for a further 30 minutes. The precipitate which has separated out is filtered off with suction and dried in vacuo. 5.0 g (100% of theory) of the title compound are obtained.

HPLC (method 1): $R_t$=3.21 min, $\lambda_{max}$=196 nm and 300 nm

MS (DCI): m/z=293 $[M+H]^+$.

$^1$H-NMR (300 MHz, DMSO-$d_6$): δ=8.19 (d, 1H), 8.07 (d, 2H), 7.98-7.91 (m, 1H), 7.80 (s, 1H).

Example 4A

5-Amino-2-iodobenzamide

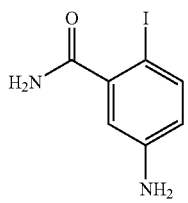

15.1 g (67 mmol) of tin(II) chloride dihydrate are added to a solution of 4.9 g (16.8 mmol) of the compound from Example 3A in 200 ml of DMF. The reaction mixture is stirred at 50° C. for one hour, and then the DMF is removed in vacuo. The residue is partitioned between 1 l of ethyl acetate and water, the phases are separated, and the organic phase is discarded. The aqueous phase is basified with 10% strength sodium hydroxide solution and again extracted with 500 ml of ethyl acetate. The product is dried over magnesium sulfate, filtered with suction and concentrated in vacuo. 3.95 g (90% of theory) of the title compound are obtained and are reacted without further purification in the next stage.

LC-MS (method 2): $R_t$=0.92 min

MS (ESI): m/z=263 $[M+H]^+$ $^1$H-NMR (400 MHz, DMSO-$d_6$): δ=5.39 (s, 2H), 6.37 (dd, 1H), 6.56 (d, 1H), 7.30 (s, 1H), 7.48 (d, 1H), 7.64 (s, 1H).

Example 5A

2-Iodo-5-[(2-phenylbutanoyl)amino]benzamide

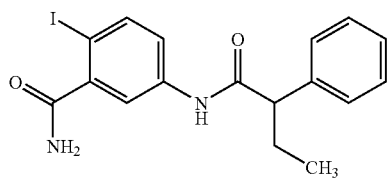

0.823 g (3.14 mmol) of the compound from Example 4A are dissolved in 10 ml of dichloromethane at RT, and 0.688 mg (3.77 mmol) of 2-phenylbutyryl chloride and 0.298 mg (3.77 mmol) of pyridine are added. The mixture is stirred at RT over after. Ethyl acetate is added, and the mixture is extracted with water. The organic phases are dried over magnesium sulfate and freed of solvent under reduced pressure. The residue is purified by chromatography on a silica gel column (mobile phase ethyl acetate:cyclohexane 2:1). 0.943 g (72% of theory) of product are obtained.

HPLC (method 1): $R_t$=4.15 min.

MS (DCI): m/z=426.3 $[M+H]^+$.

$^1$H-NMR (300 MHz, DMSO-$d_6$): δ=0.85 (t, 3H), 1.70 and 1.96-2.13 ($m_c$ and m, AB signal, 2H), 3.55 (dd, 1H), 7.20-7.42 (m, 6H), 7.47 (s, 1H), 7.65 (d, 1H), 7.74 (d, 1H), 7.79 (s, 1H), 10.25 (s, 1H).

Example 6A

Polymer-bound 2-iodo-5-nitrobenzamide
(polymer 1)

4.0 g (3.092 mmol) of Fmoc-Rink amide (0.77 mmol/g, Rapp Polymer) are mixed with 20 ml of a 4:1 mixture of DMF and piperidine. The mixture is shaken at RT for 30 min. The polymer is then filtered off with suction on a frit, washed three times with DMF and then three times with methanol and DCM alternately, and dried in vacuo. The Rink amide polymer deprotected in this way now has a loading of 0.93 mmol/g.

The deprotected Rink amide polymer is suspended in 20 ml of DCM and 2.00 g (1.55 mmol, 2 equivalents) of DIEA, and then 1.93 g (6.18 mmol, 2 equivalents) of 2-iodo-5-nitrobenzoyl chloride (Example 2A) are added. The mixture is shaken at room temperature overnight. This is followed by washing three times each with DMF, methanol and DCM. The resulting polymer 1 is dried in vacuo.

Example 7A 2-(1-Benzothien-2-yl)-5-nitrobenzamide

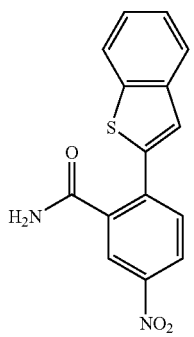

2-Iodo-5-nitrobenzamide (Example 3A; 6.56 g) is introduced into dioxane (130 ml) and sat. sodium carbonate solution (65 ml) and, after addition of benzothiophene-2-boronic acid (6.00 g) and dichlorobis(triphenylphosphine)palladium (1.58 g), stirred at 80° C. overnight. The reaction mixture is filtered through kieselguhr and washed with ethyl acetate (250 ml) and water (100 ml). The organic phase is extracted with water (three times 100 ml) and sat. sodium chloride solution (100 ml) and then dried over sodium sulfate and concentrated in a rotary evaporator. The residue is chromatographed on silica gel (cyclohexane:ethyl acetate 10:1--->pure ethyl acetate). After the product fractions have been concentrated in a rotary evaporator, the target compound is suspended in diethyl ether, filtered off with suction and dried. 4.75 g of product (64% of theory) are obtained.

LC-MS (method 4): $R_t$=2.15 min
MS (ESI): m/z=297 [M−H]−

Example 8A

5-Amino-2-(1-benzothien-2-yl)benzamide

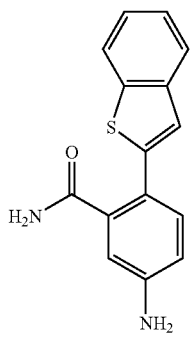

2-(1-Benzothien-2-yl)-5-nitrobenzamide (4.75 g) is introduced into THF (250 ml) and, after addition of platinum dioxide (0.57 g), hydrogenated at RT under atmospheric pressure overnight. The reaction mixture is filtered through kieselguhr and washed with THF, and the organic phase is concentrated. The residue is stirred with diethyl ether, and the crystals are filtered off with suction. They are washed with diethyl ether and a little DCM and dried. Yield 2.39 g (56% of theory).

LC-MS (method 2): $R_t$=1.91 min
MS (ESI): m/z=269 [M+H]+

Example 9A 2-(1-Benzothien-2-yl)-5-[(2-bromobutanoyl)amino]benzamide

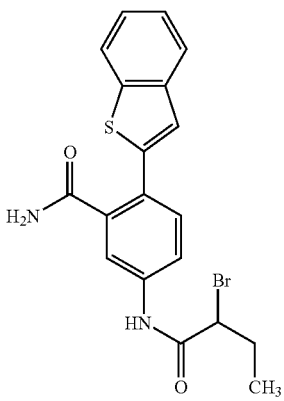

5-Amino-2-(1-benzothien-2-yl)benzamide (Example 8A, 886 mg) and triethylamine (650 mg) are introduced into DCM (20 ml) at 0° C., and 2-bromobutyryl bromide (1000 mg) is slowly added. The reaction mixture is warmed to RT and then stirred overnight. The reaction mixture is subsequently diluted with DCM (100 ml) and washed with 5% strength potassium bisulfate solution (twice 50 ml), dried (sodium sulfate) and concentrated in a rotary evaporator. The residue is chromatographed on silica gel (eluent cyclohexane-ethyl acetate 10:1 to 1:1). After concentration of the relevant fraction, 607 mg (47% of theory) of product are isolated.

LC/MS (method 2): $R_t$=2.33 min
MS (ESI): m/z=417 [M+H]+
1H-NMR (400 MHz, DMSO-$d_6$): =10.62 (br s, 1H), 7.97 (d, 2H), 7.83 (d, 1H), 7.73 (m, 2H), 7.58 (d, 1H), 7.52 (s, 1H), 7.49 (s, 1H), 7.32 (m, 2H), 4.50 (t, 1H), 2.11 (m, 1H), 1.96 (m, 1H), 0.94 (t, 3H).

EXEMPLARY EMBODIMENTS

Example 1

2-(1-Benzothien-2-yl)-5-[(2-phenylbutanoyl)amino]benzamide

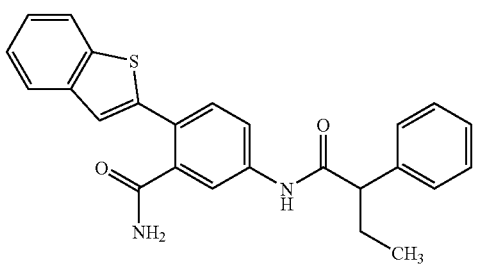

A solution of 500 mg (1.23 mmol) of the compound of Example 5A, 262 mg (1.47 mmol) of 1-benzothien-2-ylboronic acid, 1.34 ml (2.70 mmol, 2M solution in water) of sodium carbonate and 42 mg (0.061 mmol) of bis(triphenylphosphine)palladium(II) chloride in 10 ml of dimethoxyethane are stirred under reflux for 3 hours. The solution is cooled to room temperature and then partitioned between 500 ml of ethyl acetate and water, and the aqueous phase is extracted twice with 200 ml of ethyl acetate. The combined organic phases are washed with saturated sodium chloride solution, dried over magnesium sulfate, filtered with suction and concentrated. The residue is dissolved in dimethyl sulfoxide and purified by preparative RP-HPLC with acetonitrile and water. 146 mg (29% of theory) of the title compound are obtained.

LC-MS (method 2): $R_t$=2.54 min

MS (ESI): m/z=415 [M+H]$^+$ $^1$H-NMR (400 MHz, DMSO-d$_6$): δ=10.35 (s, 1H), 8.00-7.15 (m, 13H), 3.60 (m, 1H), 2.15-1.60 (m, 2H), 0.90 (t, 3H).

The enantiomers are separated by preparative HPLC on a chiral phase [DAD detection; column: KBD 5326 (based on poly(N-methacryloyl-L-leucine dicyclopropylmethylamide)), 250 mm×30 mm; eluent: ethyl acetate; flow rate: 40 ml/min; oven: 24° C.; UV detection: 254 nm].

Analytical HPLC [DAD detection; column: KBD 5326 (based on poly(N-methacryloyl-L-leucine dicyclopropylmethylamide)), 250 mm×4.6 mm; eluent: ethyl acetate; flow rate: 2 ml/min; oven: 24° C.; UV detection: 270 nm] affords the following retention times for the enantiomers:

(S)-Enantiomer 1-1:
$R_t$=3.03 min.

(R)-Enantiomer 1-2:
$R_t$=4.07 min.

Example 2

2-(6-Ethoxy-2-naphthyl)-5-[(2-phenylbutanoyl)amino]benzamide

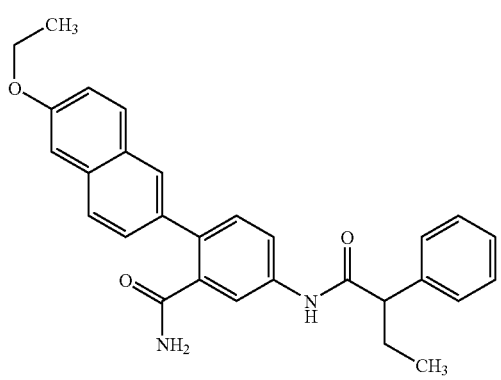

1.5 ml of saturated aqueous sodium carbonate solution, 40 mg (0.18 mmol) of 6-ethoxy-2-naphthaleneboronic acid and 14 mg (0.01 mmol) of tetrakis(triphenylphosphine)palladium are added to 50 mg (0.12 mmol) of the compound of Example 5A in 3 ml of dioxane. The mixture is stirred at 80° C. overnight and, after addition of 50 ml of ethyl acetate, extracted three times with 50 ml of water. The organic phase is dried over magnesium sulfate and freed of solvent under reduced pressure. The residue is purified by preparative HPLC (eluent: acetonitrile/water with 0.1% formic acid, gradient 10:90→95:5). 26 mg (44% of theory) of product are obtained.

HPLC (method 1): $R_t$=4.85 min.

MS (DCI): m/z=470.5 [M+NH$_4$]$^+$.

$^1$H-NMR (300 MHz, DMSO-d$_6$): δ=0.89 (t, 3H), 1.41 (t, 3H), 1.72 and 2.00-2.18 (m$_c$ and m, AB signal, 2H), 3.58 (dd, 1H), 4.15 (q, 2H), 7.15 (dd, 1H), 7.19-7.44 (m, 8H), 7.16 (dd, 1H), 7.65 (s, 1H), 7.70-7.85 (m, 5H), 10.30 (s, 1H).

Example 3

5-[(2-Phenylbutanoyl)amino]-2-(5-phenyl-2-thienyl)benzamide

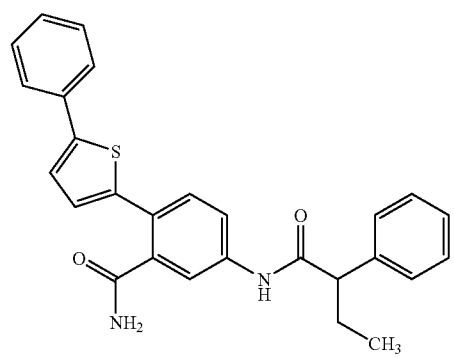

1.5 ml of saturated aqueous sodium carbonate solution, 37 mg (0.18 mmol) of 5-phenyl-2-thiopheneboronic acid and 14 mg (0.01 mmol) of tetrakis(triphenylphosphine)palladium are added to 50 mg (0.12 mmol) of the compound of Example 5A in 3 ml of dioxane. The mixture is stirred at 80° C. overnight and, after addition of 50 ml of ethyl acetate, extracted three times with 50 ml of water. The organic phase is dried over magnesium sulfate and freed of solvent under reduced pressure. The residue is purified by preparative HPLC (eluent: acetonitrile/water with 0.1% formic acid, gradient 10:90→95:5). 18 mg (30% of theory) of product are obtained.

HPLC (method 1): $R_t$=4.87 min.

MS (DCI): m/z=458.4 [M+NH$_4$]$^+$.

$^1$H-NMR (300 MHz, DMSO-d$_6$): δ=0.88 (t, 3H), 1.72 and 1.98-2.17 (m$_c$ and m, AB signal, 2H), 3.56 (dd, 1H), 7.17-7.52 (m, 12H), 7.61-7.72 (m, 4H), 7.86 (s, 1H), 10.34 (s, 1H).

Example 4

2-(1-Benzofuran-2-yl)-5-[(2-phenylbutanoyl)amino]benzamide

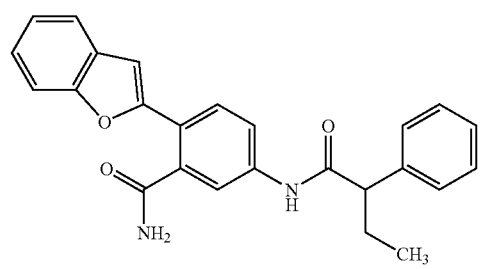

100 mg (93 μmol) of deprotected Rink amide are reacted with 54.5 mg (186 μmol) of 2-iodo-5-nitrobenzoyl chloride to give polymer 1 (Example 6A). Then, using general procedures A to D with 150.7 mg (930 μmol) of 1-benzofuran-2-ylboronic acid, 10.7 mg (9.3 μmol) of tetrakis(triphenylphosphine)palladium(0), 84.6 mg (465 μmol) of 2-phenylbutyryl chloride and 120 mg (930 μmol) of DIEA, 11.9 mg (29.9 μmol; 32% of theory) of product are obtained.

LC-MS (method 3): $R_t$=2.17 min

MS (ESI pos): m/z=399 [M+H]$^+$ $^1$H-NMR (400 MHz, DMSO-d$_6$): δ=0.88 (t, 3H), 1.72 and 2.01-2.14 (m$_c$ and m, AB signal, 2H), 3.59 (dd, 1H), 7.10 (s, 1H), 7.21-7.43 (m, 7H), 7.53-7.59 (m, 2H), 7.65 (d, 1H), 7.71-7.84 (m, 3H), 7.95 (s, 1H), 10.38 (s, 1H).

Example 5

2-(1,3-Benzodioxol-5-yl)-5-[(2-phenylbutanoyl)amino]benzamide

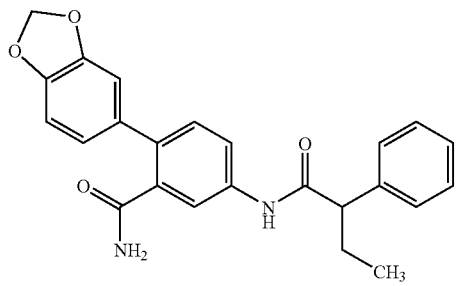

250 mg (193 μmol) of Fmoc-Rink amide (0.77 mmol/g, Rapp polymer) are reacted with 112.8 mg (385 μmol) of 2-iodo-5-nitrobenzoyl chloride to give polymer 1 (Example 6A). Then, using general procedures A to D with 320.4 mg (1.93 mmol) of 1,3-benzodioxol-5-ylboronic acid, 22.3 mg (19.3 μmol) of tetrakis(triphenylphosphine)palladium(0), 175.6 mg (965 μmol) of 2-phenylbutyryl chloride and 249 mg (1.93 mmol) of DIEA, 33.0 mg (82.1 μmol; 43% of theory) of product are obtained.

LC-MS (method 4): $R_t$=2.28 min

MS (ESI pos): m/z=403 [M+H]$^+$ $^1$H-NMR (400 MHz, CDCl$_3$): δ=7.90-6.80 (m, 11H), 6.00 (s, 2H), 5.50 (d, 2H), 3.40 (t, 1H), 2.40-1.70 (m, 2H), 0.90 (t, 3H).

Example 6

2-(1-Benzothien-3-yl)-5-[(2-phenylbutanoyl)amino]benzamide

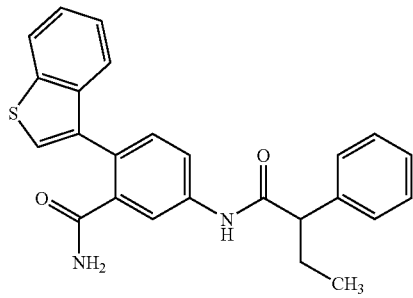

250 mg (193 μmol) of Fmoc-Rink amide (0.77 mmol/g, Rapp polymer) are reacted with 112.8 mg (385 μmol) of 2-iodo-5-nitrobenzoyl chloride to give polymer 1. Then, using general procedures A to D with 343.6 mg (1.93 mmol) of 1-benzothien-3-ylboronic acid, 22.3 mg (19.3 μmol) of tetrakis(triphenylphosphine)palladium(0), 175.6 mg (965 mmol) of 2-phenylbutyryl chloride and 249 mg (1.93 mmol) of DIEA, 18.0 mg (43.5 mmol; 23% of theory) of product are obtained.

LC-MS (method 4): $R_t$=2.50 min

MS (ESI pos): m/z=415 [M+H]$^+$ $^1$H-NMR (400 MHz, CDCl$_3$): δ=8.10-7.20 (m, 13H), 5.35 (d, 2H), 3.45 (t, 1H), 2.40-1.60 (m, 2H), 0.95 (t, 3H).

Example 7

4-[(2-Phenylbutanoyl)amino]-1,1':4', 1''-terphenyl-2-carboxamide

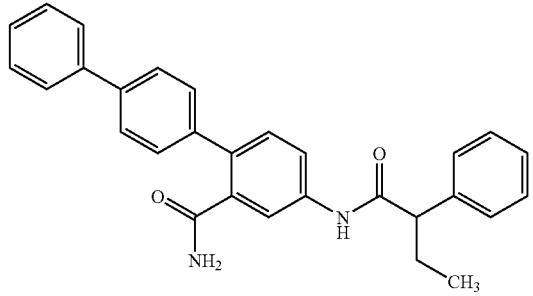

250 mg (193 μmol) of Fmoc-Rink amide (0.77 mmol/g, Rapp polymer) are reacted with 112.8 mg (385 μmol) of 2-iodo-5-nitrobenzoyl chloride to give polymer 1. Then, using general procedures A to D with 382.1 mg (1.93 mmol) of biphenyl-4-ylboronic acid, 22.3 mg (19.3 μmol) of tetrakis(triphenylphosphine)palladium(0), 175.6 mg (965 μmol) of 2-phenylbutyryl chloride and 249 mg (1.93 mmol) of DIEA, 36.3 mg (83.6 μmol; 43% of theory) of product are obtained.

LC-MS (method 4): $R_t$=2.63 min

MS (ESI pos): m/z=435 [M+H]$^+$ $^1$H-NMR (400 MHz, DMSO-d$_6$): δ=7.70-7.20 (m, 17H), 3.60 (t, 1H), 2.20-1.60 (m, 2H), 0.90 (t, 3H).

The enantiomers are separated by preparative HPLC on a chiral phase [DAD detection; column: KBD 5326 (based on poly(N-methacryloyl-L-leucine dicyclopropylmethylamide)), 250 mm×30 mm; eluent: ethyl acetate; flow rate: 40 ml/min; oven: 24° C.; UV detection: 254 nm].

Analytical HPLC [DAD detection; column: KBD 5326 (based on poly(N-methacryloyl-L-leucine dicyclopropylmethylamide)), 250 mm×4.6 mm; eluent: ethyl acetate; flow rate: 2 ml/min; oven: 24° C.; UV detection: 270 nm] affords the following retention times for the enantiomers:

(S)-Enantiomer 7-1:

$R_t$=7.67 min.

(R)-Enantiomer 7-2:

$R_t$=5.59 min.

Example 8

3'-Fluoro-4-[(2-phenylbutanoyl)amino]-1,1':4',1"-terphenyl-2-carboxamide

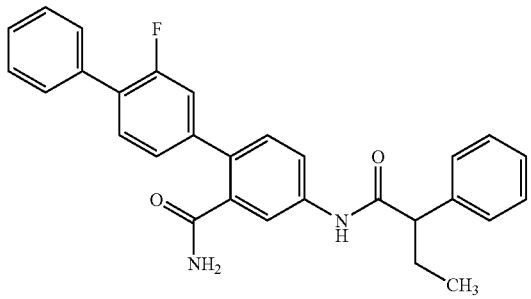

250 mg (193 µmol) of Fmoc-Rink amide (0.77 mmol/g, Rapp polymer) are reacted with 112.8 mg (385 µmol) of 2-iodo-5-nitrobenzoyl chloride to give polymer 1. Then, using general procedures A to D with 416.9 mg (1.93 mmol) of (2-fluorobiphenyl-4-yl)boronic acid, 22.3 mg (19.3 µmol) of tetrakis(triphenylphosphine)palladium(0), 175.6 mg (965 µmol) of 2-phenylbutyryl chloride and 249 mg (1.93 mmol) of DIEA, 10.0 mg (22.1 µmol; 11% of theory) of product are obtained.

LC-MS (method 4): $R_t$=2.69 min

MS (ESI pos): m/z=453 [M+H]$^+$ $^1$H-NMR (400 MHz, CDCl$_3$): δ=7.90-7.15 (m, 16H), 5.50 (d, 2H), 3.40 (t, 1H), 2.40-1.60 (m, 2H), 0.90 (t, 3H).

Example 9

2-(2-Naphthyl)-5-[(2-phenylbutanoyl)amino]benzamide

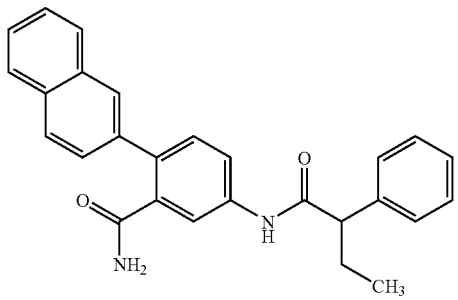

250 mg (193 µmol) of Fmoc-Rink amide (0.77 mmol/g, Rapp polymer) are reacted with 112.8 mg (385 µmol) of 2-iodo-5-nitrobenzoyl chloride to give polymer 1. Then, using general procedures A to D with 332.0 mg (1.93 mmol) of 2-naphthylboronic acid, 22.3 mg (19.3 µmol) of tetrakis(triphenylphosphine)palladium(0), 175.6 mg (965 µmol) of 2-phenylbutyryl chloride and 249 mg (1.93 mmol) of DIEA, 40.1 mg (98.3 µmol; 51% of theory) of product are obtained.

LC-MS (method 2): $R_t$=2.54 min

MS (ESI pos): m/z=409 [M+H]$^+$ $^1$H-NMR (400 MHz, DMSO-d$_6$): δ=10.30 (s, 1H), 8.00-7.20 (m, 15H), 3.60 (t, 1H), 2.20-1.60 (m, 2H), 0.90 (t, 3H).

Example 10

2-(1-Benzothien-2-yl)-5-[(2-phenylpropanoyl)amino]benzamide

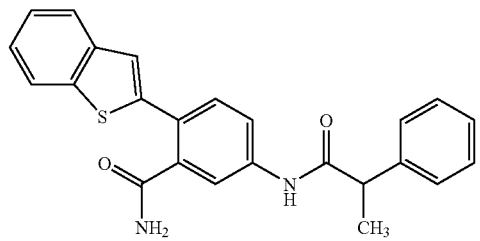

100 mg (93 µmol) of deprotected Rink amide are reacted with 54.5 mg (186 µmol) of 2-iodo-5-nitrobenzoyl chloride to give polymer 1 (Example 6A). Then, using general procedures A to D with 165.5 mg (930 mmol) of 1-benzothien-2-ylboronic acid, 10.7 mg (9.3 µmol) of tetrakis(triphenylphosphine)palladium(0), 78.1 mg (465 µmol) of 2-phenylpropanoyl chloride and 120 mg (930 µmol) of DIEA, 23.0 mg (57.4 µmol; 62% of theory) of product are obtained.

LC-MS (method 3): $R_t$=2.16 min

MS (ESI pos): m/z=401 [M+H]$^+$ $^1$H-NMR (400 MHz, DMSO-d$_6$): δ=1.42 (d, 3H), 3.87 (q, 1H), 7.22-7.28 (m, 1H), 7.31-7.43 (m, 6H), 7.45-7.56 (m, 3H), 7.70-7.77 (m, 2H), 7.82 (d, 1H), 7.90 (s, 1H), 7.95 (d, 1H), 10.32 (s, 1H).

The enantiomers are separated by preparative HPLC on a chiral phase [DAD detection; column: KBD 5326 (based on poly(N-methacryloyl-L-leucine dicyclopropylmethylamide)), 250 mm×30 mm; eluent: ethyl acetate; flow rate: 40 ml/min; oven: 24° C.; UV detection: 254 nm].

Analytical HPLC [DAD detection; column: KBD 5326 (based on poly(N-methacryloyl-L-leucine dicyclopropylmethylamide)), 250 mm×4.6 mm; eluent: ethyl acetate; flow rate: 2 ml/min; oven: 24° C.; UV detection: 270 nm] affords the following retention times for the enantiomers:

(S)-Enantiomer 10-1:
  $R_t$=3.94 min.

(R)-Enantiomer 10-2:
  $R_t$=5.95 min.

Example 11

2-(1-Benzofuran-2-yl)-5-[(2-phenylpropanoyl)amino]benzamide

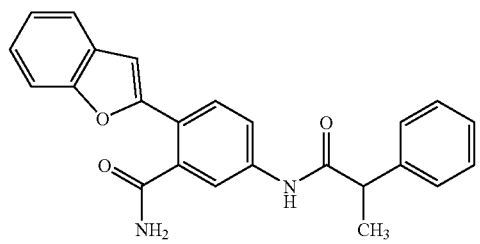

100 mg (93 µmol) of deprotected Rink amide are reacted with 54.5 mg (186 µmol) of 2-iodo-5-nitrobenzoyl chloride to give polymer 1 (Example 6A). Then, using general procedures A to D with 150.6 mg (930 μmol) of 1-benzofuran-2-ylboronic acid, 10.7 mg (9.3 μmol) of tetrakis(triphenylphosphine)palladium(0), 78.1 mg (465 μmol) of 2-phenylpropanoyl chloride and 120 mg (930 μmol) of DIEA, 11.2 mg (29.1 μmol; 31% of theory) of product are obtained.

LC-MS (method 3): $R_t$=2.09 min

MS (ESI pos): m/z=385 [M+H]$^+$

Example 12

2-(1-Benzothien-3-yl)-5-[(2-phenylpropanoyl)amino]benzamide

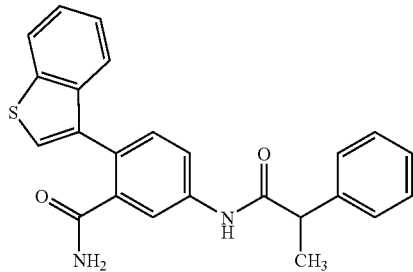

100 mg (93 μmol) of deprotected Rink amide are reacted with 54.5 mg (186 μmol) of 2-iodo-5-nitrobenzoyl chloride to give polymer 1 (Example 6A). Then, using general procedures A to D with 165.5 mg (930 μmol) of 1-benzothien-3-ylboronic acid, 10.7 mg (9.3 μmol) of tetrakis(triphenylphosphine)palladium(0), 78.1 mg (465 μmol) of 2-phenylpropanoyl chloride and 120 mg (930 μmol) of DIEA, 17.2 mg (42.9 μmol; 46% of theory) of product are obtained.

LC-MS (method 3): $R_t$=2.08 min

MS (ESI pos): m/z=401 [M+H]$^+$

Example 13

2-(1,3-Benzodioxol-5-yl)-5-[(2-phenylpropanoyl)amino]benzamide

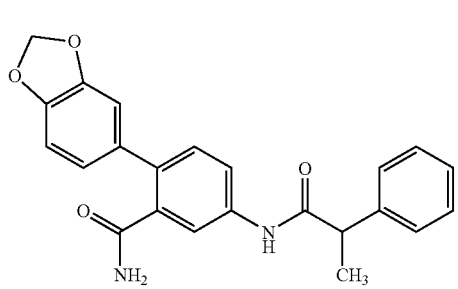

100 mg (93 μmol) of deprotected Rink amide are reacted with 54.5 mg (186 μmol) of 2-iodo-5-nitrobenzoyl chloride to give polymer 1 (Example 6A). Then, using general procedures A to D with 154.4 mg (930 μmol) of 1,3-benzodioxol-5-ylboronic acid, 10.7 mg (9.3 μmol) of tetrakis(triphenylphosphine)palladium(0), 78.1 mg (465 μmol) of 2-phenylpropanoyl chloride and 120 mg (930 μmol) of DIEA, 1.9 mg (4.9 μmol; 5% of theory) of product are obtained.

LC-MS (method 3): $R_t$=1.96 min

MS (ESI pos): m/z=389 [M+H]$^+$

Example 14

4-[(2-Phenylpropanoyl)amino]-1,1':4',1''-terphenyl-2-carboxamide

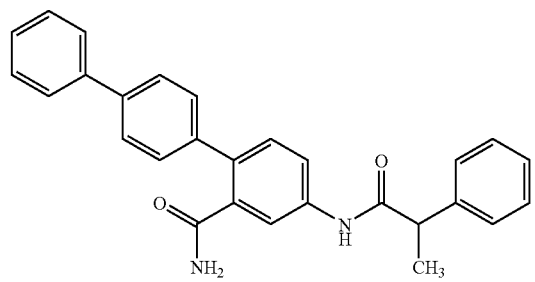

100 mg (93 μmol) of deprotected Rink amide are reacted with 54.5 mg (186 μmol) of 2-iodo-5-nitrobenzoyl chloride to give polymer 1 (Example 6A). Then, using general procedures A to D with 184.1 mg (930 μmol) of biphenyl-4-ylboronic acid, 10.7 mg (9.3 μmol) of tetrakis(triphenylphosphine)palladium(0), 78.1 mg (465 mmol) of 2-phenylpropanoyl chloride and 120 mg (930 μmol) of DIEA, 26.4 mg (62.8 μmol; 68% of theory) of product are obtained.

LC-MS (method 3): $R_t$=2.20 min

MS (ESI pos): m/z=421 [M+H]$^+$ $^1$H-NMR (400 MHz, DMSO-$d_6$): δ=1.43 (d, 3H), 3.87 (q, 1H), 5.76 (s, 2H), 7.22-7.38 (m, 1H), 7.31-7.43 (m, 7H), 7.44-7.50 (m, 4H), 7.56-7.77 (m, 7H), 10.26 (s, 1H).

Example 15

3'-Fluoro-4-[(2-phenylpropanoyl)amino]-1,1':4',1''-terphenyl-2-carboxamide

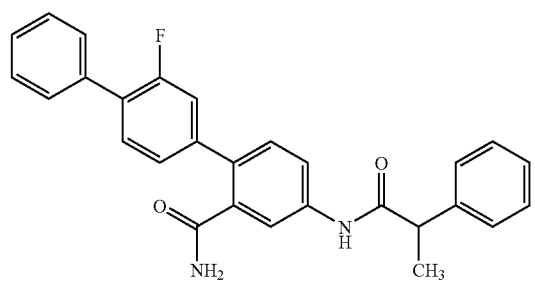

100 mg (93 μmol) of deprotected Rink amide are reacted with 54.5 mg (186 μmol) of 2-iodo-5-nitrobenzoyl chloride to give polymer 1 (Example 6A). Then, using general procedures A to D with 201.0 mg (930 μmol) of (2-fluorobiphenyl-4-yl)boronic acid, 10.7 mg (9.3 μmol) of tetrakis(triphenylphosphine)palladium(0), 78.1 mg (465 μmol) of 2-phenylpropanoyl chloride and 120 mg (930 μmol) of DIEA, 8.0 mg (18.2 μmol; 20% of theory) of product are obtained.

LC-MS (method 3): $R_t$=2.20 min

MS (ESI pos): m/z=439 [M+H]$^+$

Example 16

2-(1-Benzothien-2-yl)-5-[(2-benzylbutanoyl)amino]benzamide

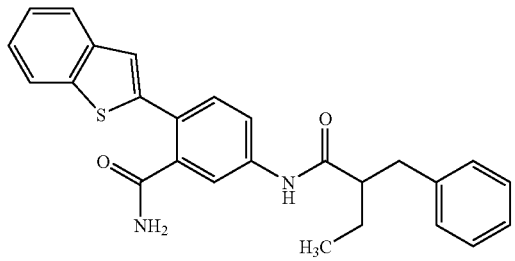

100 mg (93 μmol) of deprotected Rink amide are reacted with 54.5 mg (186 μmol) of 2-iodo-5-nitrobenzoyl chloride to give polymer 1 (Example 6A). Then, using general procedures A to D with 165.5 mg (930 μmol) of 1-benzothien-2-ylboronic acid, 10.7 mg (9.3 μmol) of tetrakis(triphenylphosphine)palladium(0), 91.1 mg (465 μmol) of 2-benzylbutyryl chloride and 120 mg (930 μmol) of DIEA, 12.1 mg (28.2 μmol; 30% of theory) of product are obtained.

LC-MS (method 3): $R_t$=2.18 min

MS (ESI pos): m/z=429 [M+H]$^+$

Example 17

2-(1-Benzothien-3-yl)-5-[(2-benzylbutanoyl)amino]benzamide

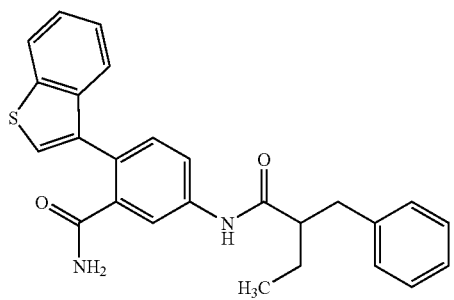

100 mg (93 μmol) of deprotected Rink amide are reacted with 54.5 mg (186 μmol) of 2-iodo-5-nitrobenzoyl chloride to give polymer 1 (Example 6A). Then, using general procedures A to D with 165.5 mg (930 μmol) of 1-benzothien-3-ylboronic acid, 10.7 mg (9.3 μmol) of tetrakis(triphenylphosphine)palladium(0), 91.1 mg (465 μmol) of 2-benzylbutyryl chloride and 120 mg (930 μmol) of DIEA, 13.6 mg (31.7 μmol; 34% of theory) of product are obtained.

LC-MS (method 3): $R_t$=2.17 min

MS (ESI pos): m/z=429 [M+H]$^+$

Example 18

2-(1,3-Benzodioxol-5-yl)-5-[(2-benzylbutanoyl)amino]benzamide

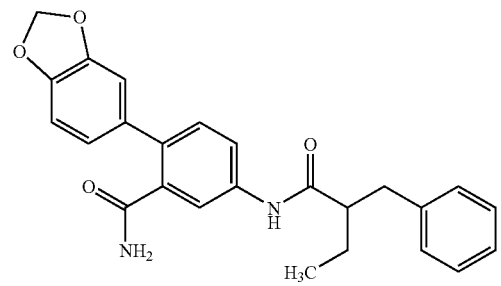

100 mg (93 μmol) of deprotected Rink amide are reacted with 54.5 mg (186 μmol) of 2-iodo-5-nitrobenzoyl chloride to give polymer 1 (Example 6A). Then, using general procedures A to D with 154.4 mg (930 μmol) of 1,3-benzodioxol-5-ylboronic acid, 10.7 mg (9.3 μmol) of tetrakis(triphenylphosphine)palladium(0), 91.1 mg (465 μmol) of 2-benzylbutyryl chloride and 120 mg (930 μmol) of DIEA, 14.9 mg (35.8 μmol; 38% of theory) of product are obtained.

LC-MS (method 3): $R_t$=2.02 min

MS (ESI pos): m/z=417 [M+H]$^+$

Example 19

4-[(2-Benzylbutanoyl)amino]-1,1':4',1''-terphenyl-2-carboxamide

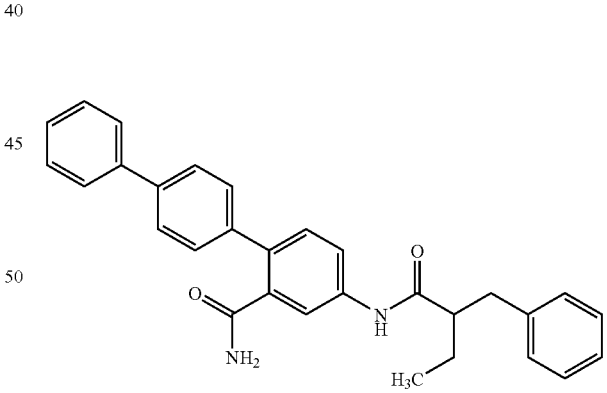

100 mg (93 μmol) of deprotected Rink amide are reacted with 54.5 mg (186 μmol) of 2-iodo-5-nitrobenzoyl chloride to give polymer 1 (Example 6A). Then, using general procedures A to D with 184.1 mg (930 μmol) of biphenyl-4-ylboronic acid, 10.7 mg (9.3 mmol) of tetrakis(triphenylphosphine)palladium(0), 91.1 mg (465 μmol) of 2-benzylbutyryl chloride and 120 mg (930 μmol) of DIEA, 4.8 mg (10.7 μmol; 12% of theory) of product are obtained.

LC-MS (method 3): $R_t$=2.28 min

MS (ESI pos): m/z=449 [M+H]$^+$

Example 20

4-[(2-Benzylbutanoyl)amino]-3'-fluoro-1,1':4',1''-terphenyl-2-carboxamide

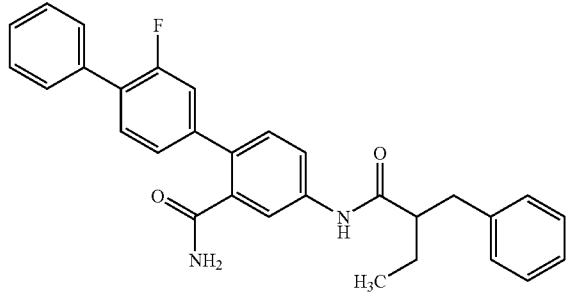

100 mg (93 µmol) of deprotected Rink amide are reacted with 54.5 mg (186 µmol) of 2-iodo-5-nitrobenzoyl chloride to give polymer 1 (Example 6A). Then, using general procedures A to D with 200.9 mg (930 µmol) of (2-fluorobiphenyl-4-yl)boronic acid, 10.7 mg (9.3 µmol) of tetrakis(triphenylphosphine)palladium(0), 91.1 mg (465 µmol) of 2-benzylbutyryl chloride and 120 mg (930 µmol) of DIEA, the product is obtained.

LC-MS (method 5): $R_t$=1.26 min

MS (ESI pos): m/z=467 [M+H]$^+$

Example 21

2-(1-Benzothien-2-yl)-5-{[2-(4-chlorophenyl)-3-methylbutanoyl]amino}benzamide

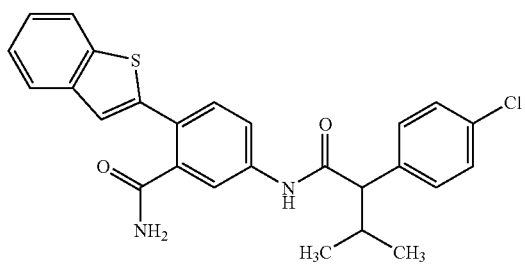

Preparation takes place in analogy to the synthesis of the compound of Example 1 from the appropriate starting compounds.

LC-MS (method 6): $R_t$=4.62 min.

MS (DCI): m/z=463.1 [M+NH$_4$]$^+$ $^1$H-NMR (400 MHz, DMSO-d$_6$): δ=0.68 (d, 3H), 1.03 (d, 3H), 2.24-2.41 (m, 1H), 3.17 (d, 1H), 7.30-7.56 (m, 9H), 7.68-7.73 (m, 2H), 7.82 (dd, 1H), 7.88-7.98 (m, 2H), 10.41 (s, 1H).

Example 22

5-[(2-Benzylbutanoyl)amino]-2-quinolin-6-ylbenzamide

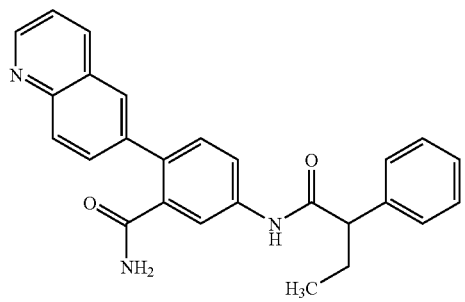

250 mg (193 µmol) of Fmoc-Rink amide (0.77 mmol/g, Rapp polymer) are reacted with 112.8 mg (385 µmol) of 2-iodo-5-nitrobenzoyl chloride to give polymer 1. Then, using general procedures A to D with 333.9 mg (1.93 mmol) of quinolin-6-ylboronic acid, 22.3 mg (19.3 µmol) of tetrakis(triphenylphosphine)palladium(0), 175.6 mg (965 µmol) of 2-phenylbutyryl chloride and 249 mg (1.93 mmol) of DIEA, 26.0 mg (64.0 µmol; 32% of theory) of product are obtained.

LC-MS (method 4): $R_t$=1.85 min

MS (ESI pos): m/z=410 [M+H]$^+$ $^1$H-NMR (400 MHz, CDCl$_3$): 8.70-7.00 (m, 14H), 6.10 (d, 2H), 3.50 (t, 1H), 2.30-1.80 (m, 2H), 0.90 (t, 3H).

Example 23

2-(7-Methoxy-2-naphthyl)-5-[(2-phenylbutanoyl)amino]benzamide

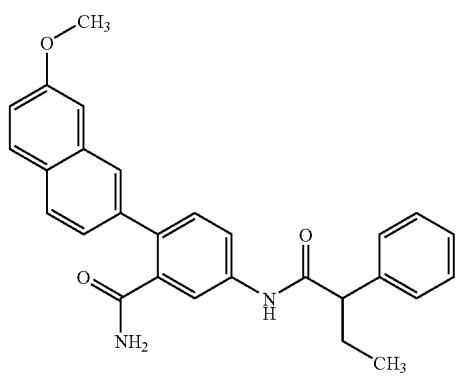

50 mg (0.12 mmol) of the compound from Example 5A are reacted with 37 mg (0.18 mmol) of 6-methoxynaphthalene-2-boronic acid in analogy to the synthesis of Example 1. 27 mg (44% of theory) of product are obtained.

HPLC (method 7): $R_t$=4.64 min

MS (DCI pos): m/z=456.3 [M+NH$_4$]$^+$ $^1$H-NMR (400 MHz, DMSO-d$_6$): δ=0.98 (t, 3H), 1.73 and 2.03-2.16 (m$_c$ and m, AB signal, 2H), 3.59 (dd, 1H), 3.88 (s, 3H), 7.17 (dd, 1H), 7.22-7.28 (m, 1H), 7.28-7.37 (m, 4H), 7.38-7.45 (m, 3H), 7.48 (dd, 1H), 7.64 (s, 1H), 7.73-7.76 (m, 2H), 7.76-7.83 (m, 3H), 10.28 (s, 1H).

Example 24

2-(1-Naphthyl)-5-[(2-phenylbutanoyl)amino]benzamide

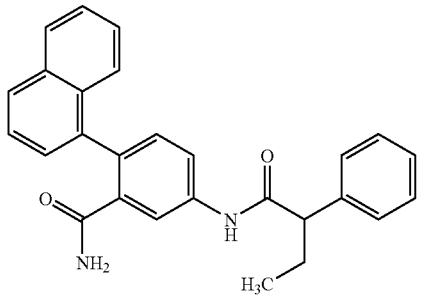

500 mg (386 µmol) of Fmoc-Rink amide (0.77 mmol/g, Rapp polymer) are reacted with 225.6 mg (770 µmol) of 2-iodo-5-nitrobenzoyl chloride to give polymer 1. Then, using general procedures A to D with 664.0 mg (3.86 mmol) of 1-naphthylboronic acid, 44.6 mg (38.6 µmol) of tetrakis(triphenylphosphine)palladium(0), 351.2 mg (1.93 mmol) of 2-phenylbutyryl chloride and 498 mg (3.86 mmol) of DIEA, 60.0 mg (147.1 µmol; 29% of theory) of product are obtained.

LC-MS (method 2): $R_f$=2.52 min

MS (ESI pos): m/z=409 [M+H]$^+$ $^1$H-NMR (400 MHz, CDCl$_3$): 8.20-7.20 (m, 14H), 5.20 (s, 2H), 3.45 (t, 1H), 2.40-1.80 (m, 2H), 0.95 (t, 3H).

Example 25

2-(1-Benzothien-2-yl)-5-{[2-(1H-1,2,4-triazol-5-ylthio)butanoyl]amino}benzamide

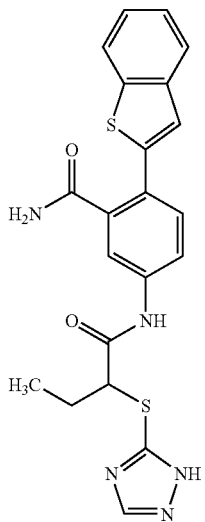

2-(1-Benzothien-2-yl)-5-[(2-bromobutanoyl)amino]benzamide (Example 9A; 50 mg) is introduced into DMF (1 ml) and, after addition of 3-mercapto-1,2,4-triazine (15 mg) and cesium carbonate (78 mg), stirred at RT overnight. The reaction mixture is mixed with ethyl acetate (50 ml) and 0.5N hydrochloric acid (50 ml), the aqueous phase is extracted with ethyl acetate (twice 50 ml), and the combined organic phases are washed with saturated sodium chloride solution (twice 100 ml). The organic phase is dried over magnesium sulfate and concentrated in a rotary evaporator. The residue is purified on a preparative HPLC. 14 mg (26% of theory) of the title compound are obtained.

LC-MS (method 6): $R_f$=1.79 min

MS (ESI): m/z=438 [M+H]$^+$ $^1$H-NMR (400 MHz, DMSO-d$_6$): δ=10.6 (s, 1H), 8.55 (s, 1H), 7.95-7.36 (m, 10H), 4.32 (t, 1H), 1.96 (m, 2H), 1.02 (t, 3H)

Example 26

2-(1-Benzothien-2-yl)-5-{[2-(1,3-thiazol-2-yl)butanoyl]amino}benzamide

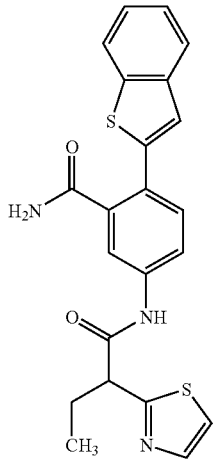

Sodium 2-(2-thiazolyl)propionate (148 mg) is introduced into DMF (5 ml), and 2-(1-benzothien-2-yl)-5-[(2-bromobutanoyl)amino]benzamide (Example 8A; 171 mg), HATU (291 mg) and 4-methylmorpholine (194 mg) are added. The reaction mixture is stirred at RT overnight. The reaction mixture is concentrated and the residue is purified by preparative HPLC. 101 mg (36% of theory) of product are isolated.

LC-MS (method 6): $R_f$=2.01 min

MS (ESI): m/z=422 [M+H]$^+$ $^1$H-NMR (400 MHz, DMSO-d$_6$): δ=10.7 (s, 1H), 7.95-7.36 (m, 11H), 4.19 (t, 1H), 2.1-1.94 (m, 2H), 0.94 (t, 3H).

Example 27

5-{[2-(3-Fluorophenyl)butanoyl]amino}-2-quinolin-3-ylbenzamide

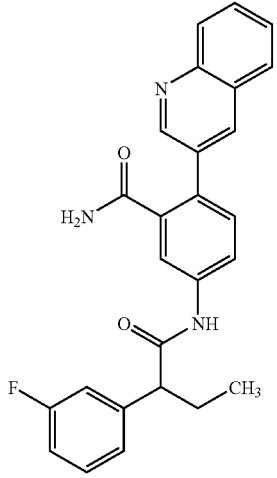

The compound is prepared from quinoline-3-boronic acid and 2-iodo-5-[(2-(3-fluorophenyl)butanoyl)amino]benzamide in analogy to Example 1 in a yield of 13.7 mg (23% of theory).

2-Iodo-5-[(2-(3-fluorophenyl)butanoyl)amino]benzamide is prepared from 5-amino-2-iodobenzamide and 2-(3-fluorophenyl)butanoic acid under standard amide coupling conditions with HATU.

LC-MS (method 4): $R_t$=2.08 min

MS (ESI): m/z=428 [M+H]$^+$ $^1$H-NMR (400 MHz, DMSO-d$_6$): δ=10.32 (s, 1H), 7.83-6.68 (m, 14H), 5.05 (d, 1H), 3.58 (t, 1H), 2.07-1.72 (m, 2H), 0.88 (t, 3H)

Example 28

2-(1-Benzothien-2-yl)-5-[(2-pyridin-3-ylbutanoyl)amino]benzamide

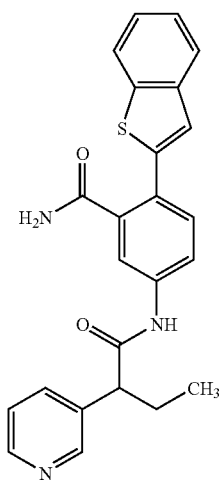

The title compound is synthesized from 5-amino-2-(1-benzothien-2-yl)benzamide and 2-(3-pyridyl)propionic acid in analogy to Example 26. 6.8 mg (8% of theory) of the title compound are obtained.

LC-MS (method 4): $R_t$=1.73 min.

$^1$H-NMR (400 MHz, DMSO-d$_6$): δ=10.78 (s, 1H), 8.88 (s, 1H), 8.75 (s, 1H), 8.40 (s, 1H), 7.87-7.04 (m, 11H), 3.95 (m, 1H), 2.16-1.84 (m, 2H), 0.91 (t, 3H).

Example 29

4-{[2-(2-Thienyl)butanoyl]amino}-1,1':4',1''-terphenyl-2-carboxamide

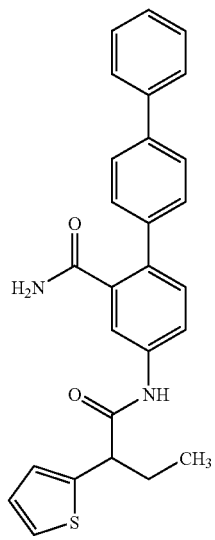

The compound is prepared from 4-amino-1,1':4',1''-terphenyl-2-carboxamide and 2-(2-thienyl)-propionic acid in analogy to Example 1 in a yield of 26%.

4-Amino-1,1':4',1''-terphenyl-2-carboxamide is prepared in analogy to the preparation of 5-amino-2-(1-benzothien-2-yl)benzamide (Example 7A and 8A).

LC-MS (method 2): $R_t$=2.73 min.
HPLC (method 1): $R_t$=4.64 min.
MS (ESI pos): m/z=441 [M+H]$^+$
$^1$H-NMR (400 MHz, DMSO-d$_6$): δ=10.39 (s, 1H), 7.73-6.98 (m, 17H), 3.93 (m, 1H), 2.06-1.78 (m, 2H), 0.91 (t, 3H).

Example 30

2-(1-Benzothien-2-yl)-5-{[2-(3-fluorophenyl)butanoyl]amino}benzamide

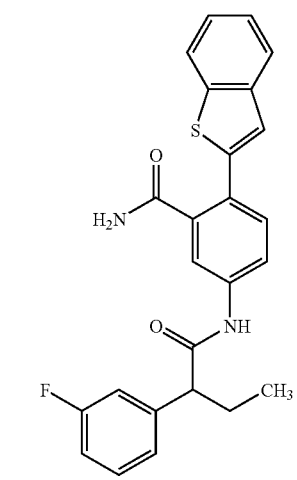

The compound is prepared in analogy to Example 26. 43.1 mg (51% of theory) of the title compound are obtained.

LC-MS (method 2): $R_t$=2.65 min.
HPLC (method 1): $R_t$=4.66 min.
MS (DCI): m/z=450 $[M+NH_4]^+$
$^1$H-NMR (400 MHz, DMSO-$d_6$): δ=10.40 (s, 1H), 7.95-7.10 (m, 14H), 3.64 (m, 1H), 2.07-1.74 (m, 2H), 0.88 (t, 3H).

The racemate is separated into the enantiomers.

Enantiomer 30-1:

$R_t$=3.22 min.

Enantiomer 30-2:

$R_t$=3.78 min.

Example 31

2-(1-Benzofuran-2-yl)-5-{[2-(2-thienyl)butanoyl]amino}benzamide

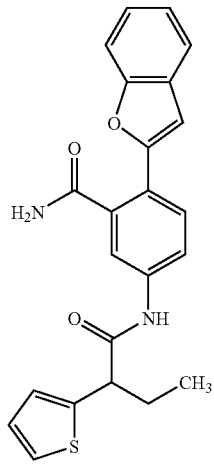

The compound is prepared in analogy to Example 26. 23.4 mg (24% of theory) of the title compound are obtained.
LC-MS (method 2): $R_t$=2.52 min.
HPLC (method 1): $R_t$=4.45 min.
MS (ESI pos): m/z=405 $[M+H]^+$
$^1$H-NMR (400 MHz, DMSO-$d_6$): δ=10.48 (s, 1H), 7.96-6.98 (m, 13H), 3.93 (m, 1H), 2.05-1.78 (m, 2H), 0.91 (t, 3H).

Example 32

2-(1-Benzothien-2-yl)-5-{[2-(2-furyl)butanoyl]amino}benzamide

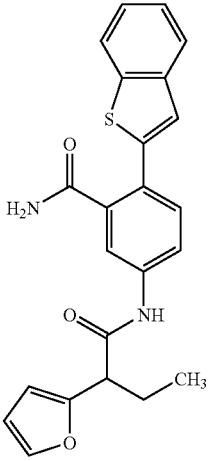

The compound is prepared in analogy to Example 26. 34.0 mg (47% of theory) of the title compound are obtained.
LC-MS (method 4): $R_t$=2.35 min.
HPLC (method 1): $R_t$=4.40 min.
MS (ESI pos): m/z=405 $[M+H]^+$
$^1$H-NMR (400 MHz, DMSO-$d_6$): δ=10.43 (s, 1H), 7.95-7.36 (m, 11H), 6.41-6.28 (m, 2H), 3.74 (m, 1H), 1.97-1.87 (m, 2H), 0.92 (t, 3H).

Example 33

2-(1-Benzothien-2-yl)-5-{[2-(3-thienyl)butanoyl]amino}benzamide

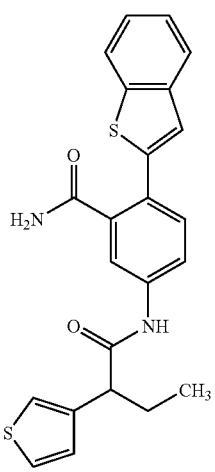

The compound is prepared in analogy to Example 26. 38.0 mg (48% of theory) of the title compound are obtained.
LC-MS (method 4): $R_t$=2.47 min.
HPLC (method 1): $R_t$=4.46 min.
MS (DCI): m/z=438 $[M+NH_4]^+$
$^1$H-NMR (400 MHz, DMSO-$d_6$): δ=10.35 (s, 1H), 7.95-7.14 (m, 13H), 3.71 (m, 1H), 2.04-1.75 (m, 2H), 0.89 (t, 3H).

Example 34

2-(1-Benzothien-2-yl)-5-{[2-(4-hydroxyphenyl)butanoyl]amino}benzamide

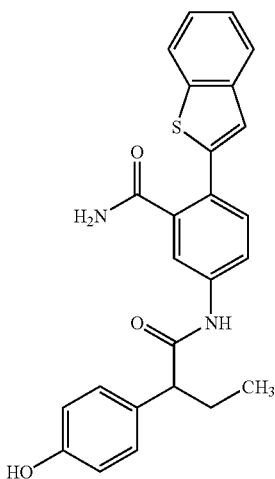

The compound is prepared in analogy to Example 26. 23.7 mg (98% of theory) of the title compound are obtained.

LC-MS (method 4): $R_t$=2.19 min.
HPLC (method 1): $R_t$=4.27 min.
MS (ESI pos): m/z=430 [M+H]$^+$
$^1$H-NMR (400 MHz, DMSO-d$_6$): δ=10.26 (s, 1H), 9.28 (s, 1H), 7.94-6.71 (m, 14H), 3.46 (m, 1H), 2.01-1.65 (m, 2H), 0.86 (t, 3H).

Example 35

2-(1-Benzothien-2-yl)-5-{[2-(2,3-dihydro-1,4-benzodioxin-6-yl)butanoyl]amino}benzamide

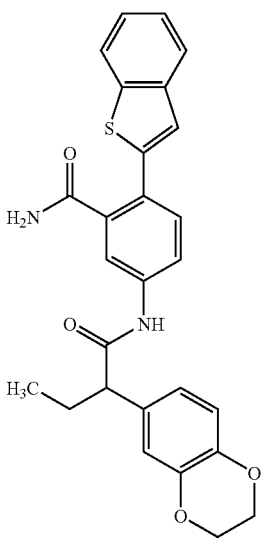

The compound is prepared in analogy to Example 26. 15.0 mg (17% of theory) of the title compound are obtained.

LC-MS (method 6): $R_t$=2.25 min.
HPLC (method 1): $R_t$=4.63 min.
MS (DCI): m/z=490 [M+NH$_4$]$^+$
$^1$H-NMR (400 MHz, DMSO-d$_6$): δ=10.29 (s, 1H), 7.96-6.81 (m, 13H), 4.21 (m, 4H), 3.46 (m, 1H), 2.01-1.66 (m, 2H), 0.86 (t, 3H).

Example 36

2-(1-Benzothien-2-yl)-5-{[2-(4-fluorophenyl)propanoyl]amino}benzamide

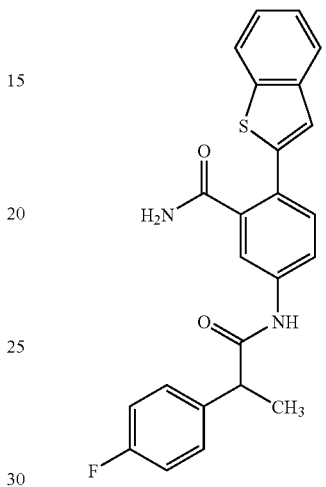

The compound is prepared in analogy to Example 26. 100.2 mg (64% of theory) of the title compound are obtained.

LC-MS (method 6): $R_t$=2.24 min.
HPLC (method 1): $R_t$=4.55 min.
MS (DCI): m/z=436 [M+NH$_4$]$^+$
$^1$H-NMR (400 MHz, DMSO-d$_6$): δ=10.34 (s, 1H), 7.95-7.17 (m, 14H), 3.87 (q, 1H), 1.43 (d, 3H).

Example 37

2-(1-Benzothien-2-yl)-5-{[2-(4-fluorophenyl)butanoyl]amino}benzamide

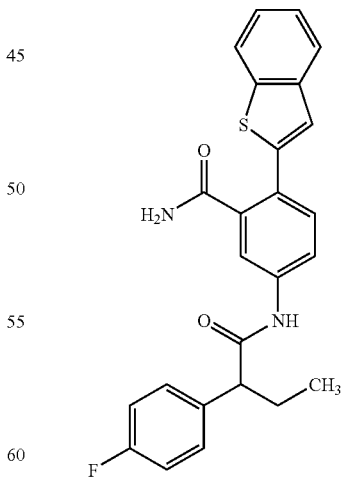

The compound is prepared in analogy to Example 26. 50.3 mg (62% of theory) of the title compound are obtained.

LC-MS (method 2): $R_t$=2.64 min.
HPLC (method 1): $R_t$=4.64 min.
MS (DCI): m/z=450 [M+NH$_4$]$^+$ ¹H-NMR (400 MHz, DMSO-d₆): δ=10.37 (s, 1H), 7.95-7.17 (m, 14H), 3.61 (m, 1H), 2.06-1.71 (m, 2H), 0.87 (t, 3H).

Enantiomer separation results in 8 mg of enantiomer 37-2 from 20 mg of racemate.

Example 38

2-(1-Benzothien-2-yl)-5-{[2-(6-chloropyridin-3-yl)propanoyl]amino}benzamide

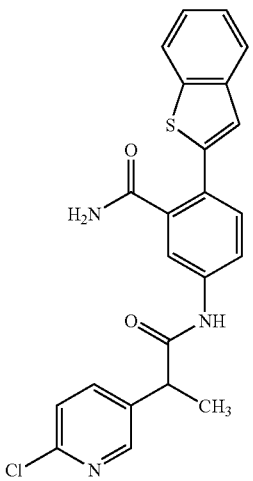

The compound is prepared in analogy to Example 26. 126.8 mg (76% of theory) of the title compound are obtained.
LC-MS (method 4): $R_t$=2.24 min.
HPLC (method 1): $R_t$=4.27 min.
MS (DCI): m/z=453 [M+NH₄]⁺

Example 39

2-(1-Benzothien-5-yl)-5-[(2-phenylbutanoyl)amino]benzamide

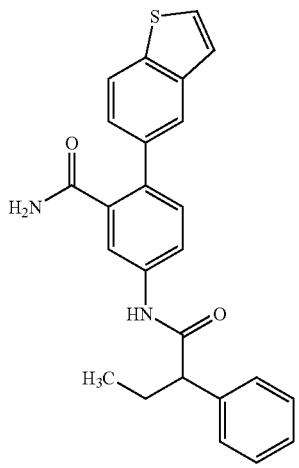

The compound is prepared in analogy to Example 1 from benzothiophene-5-boronic acid. 44.2 mg (87% of theory) of the title compound are obtained.
LC-MS (method 4): $R_t$=2.32 min.
HPLC (method 1): $R_t$=4.68 min.
MS (DCI): m/z=432 [M+NH₄]⁺
¹H-NMR (400 MHz, DMSO-d₆): δ=10.35 (s, 1H), 7.94-7.25 (m, 15H), 3.60 (m, 1H), 2.08-1.72 (m, 2H), 0.88 (t, 3H).

Enantiomer separation results in 77 mg of enantiomer 39-2 from 160 mg of racemate.

Enantiomer 39-2:
$R_t$=5.61 min.

Example 40

2-(1-Benzothien-2-yl)-5-{[2-(4-cyanophenyl)butanoyl]amino}benzamide

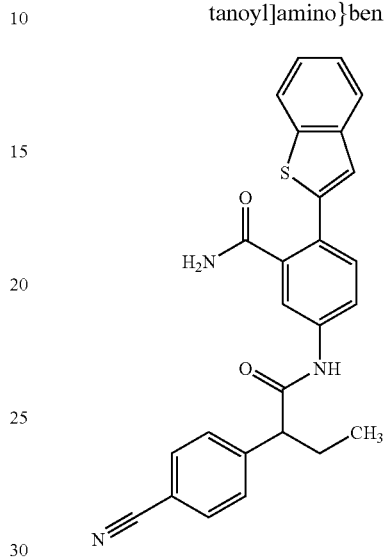

The compound is prepared in analogy to Example 26. 22.4 mg (27% of theory) of the title compound are obtained.
LC-MS (method 2): $R_t$=2.50 min.
HPLC (method 1): $R_t$=4.66 min.
MS (ESI pos): m/z=440 [M+H]⁺
¹H-NMR (400 MHz, DMSO-d₆): δ=10.45 (s, 1H), 7.94-7.36 (m, 14H), 3.72 (m, 1H), 2.09-1.75 (m, 2H), 0.89 (t, 3H).

Example 41

2-(1-Benzothien-2-yl)-5-{[2-(2-thienyl)butanoyl]amino}benzamide

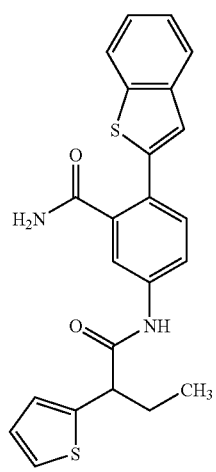

The compound is prepared in analogy to Example 26. 12.0 mg (15% of theory) of the title compound are obtained.
LC-MS (method 4): $R_t$=2.46 min.

¹H-NMR (400 MHz, DMSO-$d_6$): δ=10.46 (s, 1H), 7.95-6.98 (m, 13H), 3.93 (m, 1H), 2.05-1.78 (m, 2H), 0.91 (t, 3H).

The racemate is separated into the enantiomers.

Enantiomer 41-1:
$R_t$=3.84 min.

Enantiomer 41-2:
$R_t$=5.61 min.

B) ASSESSMENT OF THE PHYSIOLOGICAL ACTIVITY

The suitability of the compounds of the invention for the treatment of cardiovascular disorders can be shown in the following assay systems:

Functional Reporter Assay for High Throughput Screening of IL8B Receptor Antagonists CHO cells with mitochondrially localized aequorin are stably transfected with the human IL8B receptor and the G-alpha-16 protein. Activation of the IL8B receptor with IL8 or an endogenous P2Y receptor with ATP leads to $Ca^{2+}$ release. This intracellular $Ca^{2+}$ transient can be detected by bioluminescence with mitochondrially localized aequorin. IL8-induced $Ca^{2+}$ transients are inhibited by IL8B receptor antagonists. Substances which also inhibit ATP-induced $Ca^{2+}$ transients are nonspecific.

2000 cells in 25 µl of complete medium with 10% FCS per well of a 384-well multititer plate are incubated at 37° C. and 5% $CO_2$ for 24 h. After removal of the medium, 30 µl of an 11.8 µM coelenterazine solution in 2 mM Ca-Tyrode are added, and the cells are incubated at 37° C. in 5% $CO_2$ for a further 4 hours. 10 µl of test substance in 2 mM Ca-Tyrode/0.1% BSA are added, and the cells are incubated at room temperature for 5 minutes. The IL8B receptor is activated by adding 25 µl of a 0.78-2.6 nM IL8 solution in 2 mM Ca-Tyrode/0.1% BSA, or the endogenous P2Y receptor is activated by adding 25 µl of a 7.8-26 µM ATP solution in 2 mM Ca-Tyrode. The bioluminescence is recorded at the same time. $IC_{50}$ values are calculated from dose-response plots using the Marquardt-Levenberg fit (Table A).

TABLE A

| Ex. No. | $IC_{50}$ [µM] |
|---|---|
| 1-2 | 0.1 |
| 2 | 0.2 |
| 26 | 0.082 |
| 29 | 0.092 |
| 30 | 0.077 |
| 35 | 0.074 |
| 39-2 | 0.064 |

IL-8-Induced ROS (Reactive Oxygen Species) Assay with Primary Human PMNLs

Human PMNLs are isolated from fresh blood from volunteer donors (as described in *Current Protocols in Immunology*, Vol. I, Suppl. 1, Unit 7.23.1). The isolated cells are stored in DMEM (Dulbecco's minimal essential medium) at 4-8° C. before they are used.

Test substances, luminol (50 µM), Horse Radish Peroxidase (HRP; 1 U/ml) and recombinant human IL-8 (10-50 nM) are incubated with the PMN cell suspension, and the emitted luminescence is measured without delay as RLUs (relative light units) in a luminometer. This is regarded as a measure of the IL-8-induced ROS generation. The area under the corresponding curve is used in order to determine the inhibitory activity and the half-maximum inhibitory concentration of the tested substances.

IL8 Binding Affinity

Cell culture: CHO cells which have been transfected with the human IL8 receptor B are cultured in DMEM medium with 10% FCS, penicillin (100 units/ml), streptomycin (100 µg/ml) and 0.4 mg/ml G418.

Membrane preparation: Cells are harvested subconfluently with trypsin and centrifuged at 500×g for 5 min. The cell pellet is washed with PBS and then taken up in ice-cold assay buffer (50 mM Tris-HCl, 10 mM EDTA, 10 mM $MgCl_2$, pH 7.4 including once protease inhibitor cocktail (#1873580, Roche)). The cells are then homogenized on ice using a Polytron for 30 seconds and centrifuged at 500×g at 4° C. for 10 min in order to remove the cell nuclei. The supernatant is then centrifuged at 100 000×g (30 min, 4° C.) and the membrane pellet is resuspended in assay buffer. The membrane preparation is frozen at −80° C., and the protein content is determined by means of the BCA assay (Pierce).

Receptor binding: Receptor membranes (1 µg) are incubated with 0.2 n$M^{125}$I-labeled IL8 (Amersham) in assay buffer in the presence and absence of test substance at room temperature for 2 h. Receptor-bound IL8 is measured in a Wallac scintillation counter by adding WGA SPA beads (Amersham).

IL-8-Peritonitis Model (In Vivo Assay)

The IL-8-induced migration of neutrophilic granulocytes from the blood into the mouse peritoneum is measured. For this purpose, female BALB/c mice (n=6-8) are injected i.p. with human recombinant IL-8 [10 ug/kg, 25 ml/kg]. Two hours later, the animals are sacrificed and the abdominal cavity is rinsed out to obtain the cells which have migrated in. Neutrophilic granulocytes which have migrated in are labeled with fluorescence-labeled antibodies which bind to the cell surface antigen Ly-6G, and quantified by means of FACS.

Substances are administered 30 min (orally) [10 ml/kg] or 10 min (i.v.) [5 ml/kg] before the IL-8 stimulation. The proportion of neutrophils as a percentage of the total number of cells is determined for the placebo-treated unstimulated control group, the IL-8-stimulated control group and for the substance-treated animals. The percentage inhibition caused by substance administration, and the significance (t test) of the IL-8-induced neutrophil migration is calculated relative to the IL-8-treated control animals.

Atherosclerosis Model in Mice (In Vivo Assay)

The antiatheroaclerotic effect of IL-8 receptor antagonists is determined by using animal models generally accepted in research, such as the ApoE knockout mouse (Reddick, R. L., et al., *Arterioscler. Thromb.* 1994, 14, 141-147) or the LDL receptor knockout mouse (Ishibashi, S., et al., *Proc. Natl. Acad. Sci. USA* 1993, 91, 4431-4435). In all the models, either the anti-atherosclerotic effect is determined indirectly in short-term investigations (1-2 months) through an altered gene expression of relevant marker genes in atherosclerosis-susceptible tissue, or the development of atherosclerotic plaques is determined directly in long-term investigations (3-6 months) with the aid of histological techniques.

Rat HF Model (In Vivo Assay)

Male Wistar rats (300 g; Harlan/Winkelmann) are anesthetized with 5% isoflurane, intubated and ventilated with 2% isoflurane, oxygen, nitrous oxide using a ventilation pump (ugo basile 7025 rodent; 7 ml/stroke; 50 strokes per min). The thorax is opened and the LAD (left descending coronary artery) on the heart is ligated with a thread (PROLENE 1 metric 5-0 ETHICON1H) passed underneath. The animal is closed again with sutures, the wound is dressed and the anesthesia is terminated. The oral treatment with IL-8 receptor antagonists starts 1-2 days after the occlusion of the LAD.

ECG and echocardiographic investigations are carried out over several weeks or months at regular intervals in order to analyze the development of heart failure, with and without Il-8 receptor antagonists, in the rats. Blood samples are regularly taken in order to determine biomarkers (e.g. BNP) which are a clinically accepted measure of the development of heart failure. At the end of the study, the contractility of the heart is determined in vivo on the animals under isoflurane anesthesia (2% isoflurane, oxygen, nitrous oxide) using a Millar pressure catheter, and the hearts are removed and characterized histologically.

Further HF in vivo assay systems are known from the literature: Braun A. et al., Circ. Res., 90, 270-6 (2002); Wang Q.-D. et al., J. Pharmacol. Toxicol. Methods, 50, 163-74 (2004); Monnet E. et al., Ann. Thorac. Surg., 79, 1445-53 (2005); Caligiuriet G. et al, Proc. Natl. Acad. Sci., 96, 6920-4 (1999).

C) EXEMPLARY EMBODIMENTS OF PHARMACEUTICAL COMPOSITIONS

The substances of the invention can be converted into pharmaceutical preparations in the following ways:

Tablet:

Composition:
100 mg of the compound of Example 1, 50 mg of lactose (monohydrate), 50 mg of corn starch, 10 mg of polyvinylpyrolidone (PVP 25) (BASF, Germany) and 2 mg of magnesium stearate.

Tablet weight 212 mg. Diameter 8 mm, radius of curvature 12 mm.

Production:
The mixture of the compound of Example 1, lactose and starch is granulated with a 5% strength solution (m/m) of PVP in water. The granules are dried and then mixed with the magnesium stearate for 5 min. This mixture is compressed with a conventional tablet press (see above for format of the tablet).

Oral Suspension:

Composition:
1000 mg of the compound of Example 1, 1000 mg of ethanol (96%), 400 mg of Rhodigel (xanthan gum from FMC, USA) and 99 g of water.

10 ml of oral suspension are equivalent to a single dose of 100 mg of the compound of the invention.

Production:
The Rhodigel is suspended in ethanol, and the compound of Example 1 is added to the suspension. The water is added while stirring. The mixture is stirred for about 6 h until the swelling of the Rhodigel is complete.

Solution which can be Administered Intravenously:

Composition:
1 mg of the compound of Example 1, 15 g of polyethylene glycol 400 and 250 g of water for injections.

Production:
The compound of Example 1 is dissolved together with polyethylene glycol 400 in the water with stirring. The solution is sterilized by filtration (pore diameter 0.22 μm) and dispensed under aseptic conditions into heat-sterilized infusion bottles. These are closed with infusion stoppers and crimped caps.

The invention claimed is:

1. A compound of the formula

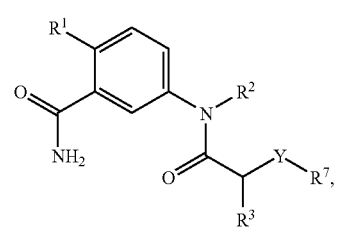

(Ia)

in which

Y is a bond, methanediyl, sulfur or oxygen;

$R^1$ is biphenyl-4-yl, where 1 to 3 carbon atoms in biphenyl-4-yl may be replaced by nitrogen, or $R^1$ is 1,3-benzodioxol-5-yl or 2,3-dihydro-1,4-benzodioxin-5-yl, or $R^1$ is a group of the formula

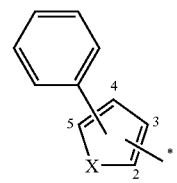

where

X is N, O or S,

* is the point of attachment to the carbon atom, and the phenyl ring is linked via position 4 or 5 when the five-membered ring is linked via position 2 to the carbon atom, or the phenyl ring is linked via position 5 when the five-membered ring is linked via position 3 to the carbon atom, or $R^1$ is naphth-1-yl or naphth-2-yl, where 1 carbon atom in naphth-1-yl and naphth-2-yl may be replaced by nitrogen, or $R^1$ is a group of the formula

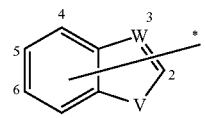

where

W is C or N,

V is N, O or S,

* is the point of attachment to the carbon atom, and the group is linked via position 2, 3, 5 or 6 to the carbon atom, or $R^1$ is a group of the formula

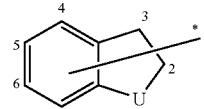

where

U is N, O or S,

* is the point of attachment to the carbon atom, and the group is linked via position 2, 3, 5 or 6 to the carbon atom, where $R^1$ may be substituted by 1 to 3 substituents, where the substituents are selected independently of one another from the group consisting of hydroxy, amino, halogen, cyano, trifluoromethyl, trifluoromethoxy, $C_1$-$C_6$-alkyl, $C_1$-$C_6$-alkoxy, $C_1$-$C_6$-alkylamino, hydroxycarbonyl, $C_1$-$C_6$-alkoxycarbonyl, aminocarbonyl, $C_1$-$C_6$-alkylaminocarbonyl, $C_1$-$C_6$-alkylcarbonyl and $C_1$-$C_6$-alkylcarbonylamino;

$R^2$ is hydrogen, $C_1$-$C_6$-alkyl or $C_3$-$C_7$-cycloalkyl;

$R^3$ is $C_3$-$C_7$-cycloalkyl or optionally up to pentafluoro-substituted $C_1$-$C_4$-alkyl; and $R^7$ is a group of the formula

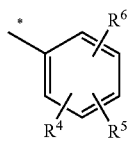

where

* is the point of attachment to Y, $R^4$, $R^5$ and $R^6$ are independently of one another hydrogen, hydroxy, amino, halogen, cyano, trifluoromethyl, trifluoromethoxy, $C_1$-$C_6$-alkyl, $C_1$-$C_6$-alkoxy, $C_1$-$C_6$-alkylamino, $C_3$-$C_7$-cycloalkyl, 5- to 7-membered heterocyclyl, $C_6$-$C_{10}$-aryl, 5- or 6-membered heteroaryl, hydroxycarbonyl, $C_1$-$C_6$-alkoxycarbonyl, aminocarbonyl, $C_1$-$C_6$-alkylaminocarbonyl, $C_1$-$C_6$-alkylcarbonyl carbonyl, $C_1$-$C_6$-alkylaminocarbonyl, $C_1$-$C_6$-alkylcarbonyl or $C_1$-$C_6$-alkylcarbonylamino, in which cycloalkyl, heterocyclyl, aryl and heteroaryl may be substituted by 1 to 3 substituents, where the substituents are selected independently of one another from the group consisting of hydroxy, amino, halogen, cyano, trifluoromethyl, trifluoromethoxy, $C_1$-$C_6$-alkyl, $C_1$-$C_6$-alkoxy, $C_1$-$C_6$-alkylamino, hydroxycarbonyl, $C_1$-$C_6$-alkoxycarbonyl, aminocarbonyl, $C_1$-$C_6$-alkylamino-carbonyl, $C_1$-$C_6$-alkylcarbonyl and $C_1$-$C_6$-alkylcarbonylamino, or $R^4$ and $R^5$ are linked to adjacent carbon atoms and form a —O—$CH_2$—$CH_2$—O-bridge, or $R^7$ is a 5- or 6-membered heteroaryl, in which heteroaryl may be substituted by 1 to 3 substituents, where the substituents are selected independently of one another from the group consisting of hydroxy, amino, halogen, cyano, trifluoromethyl, trifluoromethoxy, $C_1$-$C_6$-alkyl, $C_1$-$C_6$-alkoxy and $C_1$-$C_6$-alkylamino;

or a salt thereof.

2. The compound as claimed in claim 1, which corresponds to the formula

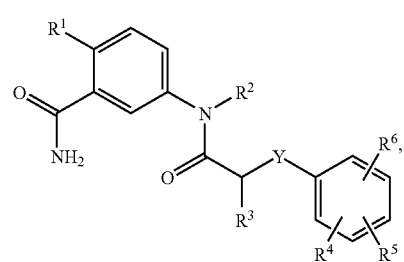

in which

Y is a bond or methanediyl;

$R^1$ is biphenyl-4-yl, 1,3-benzodioxol-5-yl, 2,3-dihydro-1,4-benzodioxin-5-yl, 5-phenylthien-2-yl, 5-phenylfuran-2-yl, naphth-1-yl, naphth-2-yl, quinolin-6-yl, 1-benzothien-2-yl, 1-benzothien-3-yl, 1-benzothien-5-yl, 1-benzothien-6-yl, 1-benzofuran-2-yl or 1-benzofuran-3-yl, where biphenyl-4-yl, 1,3-benzodioxol-5-yl, 2,3-dihydro-1,4-benzodioxin-5-yl, 5-phenylthien-2-yl, 5-phenylfuran-2-yl, naphth-1-yl, naphth-2-yl, quinolin-6-yl, 1-benzothien-2-yl, 1-benzothien-3-yl, 1-benzothien-5-yl, 1-benzothien-6-yl, 1-benzofuran-2-yl and 1-benzofuran-3-yl may be substituted by 1 to 3 substituents, where the substituents are selected independently of one another from the group consisting of hydroxy, amino, halogen, cyano, trifluoromethyl, trifluoromethoxy, $C_1$-$C_6$-alkyl, $C_1$-$C_6$-alkoxy, $C_1$-$C_6$-alkylamino, hydroxycarbonyl, $C_1$-$C_6$-alkoxycarbonyl, aminocarbonyl, $C_1$-$C_6$-alkylaminocarbonyl, $C_1$-$C_6$-alkylcarbonyl and $C_1$-$C_6$-alkylcarbonylamino;

$R^2$ is hydrogen or $C_1$-$C_6$-alkyl;

$R^3$ is $C_3$-$C_7$-cycloalkyl or optionally up to pentafluoro-substituted $C_1$-$C_4$-alkyl; and $R^4$, $R^5$ and $R^6$ are independently of one another hydrogen, hydroxy, amino, halogen, cyano, trifluoromethyl, trifluoromethoxy, $C_1$-$C_6$-alkyl, $C_1$-$C_6$-alkoxy, $C_1$-$C_6$-alkylamino, $C_3$-$C_7$-cycloalkyl, 5- to 7-membered heterocyclyl, $C_6$-$C_{10}$-aryl, 5- or 6-membered heteroaryl, hydroxycarbonyl, $C_1$-$C_6$-alkoxycarbonyl, aminocarbonyl, $C_1$-$C_6$-alkyl-aminocarbonyl, $C_1$-$C_6$-alkylcarbonyl or $C_1$-$C_6$-alkylcarbonylamino, in which cycloalkyl, heterocyclyl, aryl and heteroaryl may be substituted by 1 to 3 substituents, where the substituents are selected independently of one another from the group consisting of hydroxy, amino, halogen, cyano, trifluoromethyl, trifluoromethoxy, $C_1$-$C_6$-alkyl, $C_1$-$C_6$-alkoxy, $C_1$-$C_6$-alkylamino, hydroxycarbonyl, $C_1$-$C_6$-alkoxycarbonyl, aminocarbonyl, $C_1$-$C_6$-alkylaminocarbonyl, $C_1$-$C_6$-alkylcarbonyl and $C_1$-$C_6$-alkylcarbonylamino.

3. The compound as claimed in claim 1, characterized in that

Y is a bond or methanediyl;

$R^1$ is biphenyl-4-yl, 1,3-benzodioxol-5-yl, 2,3-dihydro-1,4-benzodioxin-5-yl, 5-phenylthien-2-yl, 5-phenylfuran-2-yl, naphth-1-yl, naphth-2-yl, quinolin-6-yl, 1-benzothien-2-yl, 1-benzothien-3-yl, 1-benzothien-5-yl, 1-benzothien-6-yl, 1-benzofuran-2-yl or 1-benzofuran-3-yl, where biphenyl-4-yl, 1,3-benzodioxol-5-yl, 2,3-dihydro-1,4-benzodioxin-5-yl, 5-phenylthien-2-yl, 5-phenylfuran-2-yl, naphth-1-yl, naphth-2-yl, quinolin-6-yl, 1-benzothien-2-yl, 1-benzothien-3-yl, 1-benzothien-5-yl, 1-benzothien-6-yl, 1-benzofuran-2-yl and 1-benzofuran-3-yl may be substituted by 1 to 3 substituents, where the substituents are selected independently of one another from the group consisting of hydroxy, amino, halogen, cyano, trifluoromethyl, trifluoromethoxy, $C_1$-$C_6$-alkyl, $C_1$-$C_6$-alkoxy, $C_1$-$C_6$-alkylamino, hydroxycarbonyl, $C_1$-$C_6$-alkoxycarbonyl, aminocarbonyl, $C_1$-$C_6$-alkylaminocarbonyl, $C_1$-$C_6$-alkylcarbonyl and $C_1$-$C_6$-alkylcarbonylamino;

$R^2$ is hydrogen or $C_1$-$C_6$-alkyl;

$R^3$ is $C_3$-$C_7$-cycloalkyl or optionally up to pentafluoro-substituted $C_1$-$C_4$-alkyl; and $R^4$, $R^5$ and $R^6$ are independently of one another hydrogen, halogen, cyano, trifluoromethyl, trifluoromethoxy, $C_1$-$C_6$-alkyl, $C_3$-$C_7$-cycloalkyl, hydroxycarbonyl, $C_1$-$C_6$-alkoxycarbonyl, aminocarbonyl, $C_1$-$C_6$-alkylaminocarbonyl, $C_1$-$C_6$-alkylcarbonyl or $C_1$-$C_6$-alkylcarbonylamino, in which cycloalkyl may be substituted by 1 to 3 substituents, where the substituents are selected independently of one another from the group consisting of hydroxy, amino, halogen, cyano, trifluoromethyl, trifluoromethoxy, $C_1$-$C_6$-alkyl, $C_1$-$C_6$-alkoxy, $C_1$-$C_6$-alkylamino, hydroxycarbonyl, $C_1$-$C_6$-alkoxycarbonyl, aminocarbonyl, $C_1$-$C_6$-alkylaminocarbonyl, $C_1$-$C_6$-alkylcarbonyl and $C_1$-$C_6$-alkylcarbonylamino.

4. The compound as claimed in claim 1, characterized in that

Y is a bond or methanediyl;

$R^1$ for biphenyl-4-yl, 5-phenylthien-2-yl, naphth-2-yl, quinolin-6-yl, 1-benzothien-2-yl or 1-benzofuran-2-yl, where biphenyl-4-yl and naphth-2-yl may be substituted by 1 to 2 substituents, where the substituents are selected independently of one another from the group consisting of fluorine, chlorine, methoxy and ethoxy;

$R^2$ is hydrogen;

$R^3$ is methyl, ethyl or isopropyl; and $R^4$, $R^5$ and $R^6$ are independently of one another hydrogen or halogen.

5. A method for preparing a compound of the formula (Ia) as claimed in claim 1, characterized in that

[A] a compound of the formula

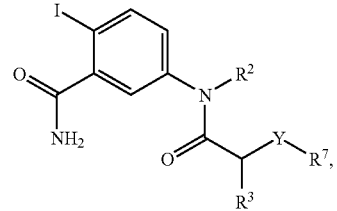

(II)

in which

Y, $R^2$, $R^3$ and $R^7$ have the meaning indicated in claim 1, is reacted with a compound of the formula

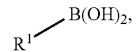

(III)

in which $R^1$ has the meaning indicated in claim 1, or

[B] a compound of the formula

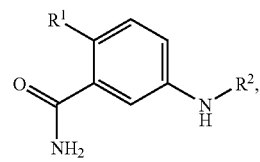

(IV)

in which $R^1$ and $R^2$ have the meaning indicated in claim 1, is reacted with a compound of the formula

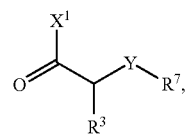

(V)

in which

Y, $R^3$ and $R^7$ have the meaning indicated in claim 1, and $X^1$ is halogen, preferably iodine or bromine, or hydroxy.

6. A pharmaceutical composition comprising a compound as claimed in any of claims 1 to 4 in combination with at least one inert, nontoxic, pharmaceutically suitable excipient.

7. A method for treating arteriosclerosis in humans and animals by administering an effective amount of at least one compound as claimed in any of claims 1 to 4.

* * * * *